(12) United States Patent
Klein

(10) Patent No.: US 8,512,279 B2
(45) Date of Patent: Aug. 20, 2013

(54) SYRINGE

(75) Inventor: Cornelis Kees Klein, Auckland (NZ)

(73) Assignee: Klein Medical Limited, Auckland (NL)

( * ) Notice: Subject to any disclaimer, the term of this patent is extended or adjusted under 35 U.S.C. 154(b) by 445 days.

(21) Appl. No.: 11/564,348

(22) Filed: Nov. 29, 2006

(65) Prior Publication Data

US 2007/0121230 A1    May 31, 2007

(51) Int. Cl.
*A61M 31/00* (2006.01)
*A61M 37/00* (2006.01)
*A61M 5/00* (2006.01)

(52) U.S. Cl.
USPC ......... 604/93.01; 606/181; 606/187; 606/232

(58) Field of Classification Search
None
See application file for complete search history.

(56) References Cited

U.S. PATENT DOCUMENTS

| | | | |
|---|---|---|---|
| 4,021,124 A | 5/1977 | Sarstedt | |
| 4,158,505 A | 6/1979 | Mathisen et al. | |
| 4,332,471 A | 6/1982 | Gross | |
| 4,832,491 A | 5/1989 | Sharpe et al. | |
| 5,066,859 A | 11/1991 | Karkar et al. | |
| 5,112,327 A * | 5/1992 | Iinuma et al. | 604/413 |
| 5,249,584 A * | 10/1993 | Karkar et al. | 600/578 |
| 5,345,395 A | 9/1994 | Griner | |
| 5,357,343 A | 10/1994 | Lowne et al. | |
| 5,407,638 A * | 4/1995 | Wang | 422/82.09 |
| 5,437,076 A | 8/1995 | Vasquez | |
| 5,602,647 A | 2/1997 | Xu et al. | |
| 5,647,359 A | 7/1997 | Kohno et al. | |
| 5,652,654 A | 7/1997 | Asimopoulos | |
| 5,658,532 A | 8/1997 | Kurosaki et al. | |
| 5,684,582 A | 11/1997 | Eastman et al. | |
| 5,689,110 A | 11/1997 | Dietz et al. | |
| 5,772,443 A | 6/1998 | Lampotang et al. | |
| 5,818,048 A | 10/1998 | Sodickson et al. | |
| 6,068,615 A * | 5/2000 | Brown et al. | 604/207 |
| 6,111,639 A | 8/2000 | Reduto | |
| 6,352,523 B1 | 3/2002 | Brown et al. | |
| 6,493,069 B1 | 12/2002 | Nagashimada et al. | |
| 6,643,016 B2 | 11/2003 | Garver et al. | |
| 6,685,678 B2 | 2/2004 | Evans et al. | |
| 6,773,675 B2 | 8/2004 | Cocola et al. | |
| 6,847,899 B2 | 1/2005 | Allgeyer | |
| 6,973,158 B2 | 12/2005 | Besson | |
| 7,002,670 B2 | 2/2006 | Wariar et al. | |
| 7,015,484 B2 | 3/2006 | Gillispie et al. | |
| 7,041,085 B2 * | 5/2006 | Perez et al. | 604/198 |
| 7,154,599 B2 * | 12/2006 | Adams et al. | 356/317 |
| 7,238,942 B2 | 7/2007 | Goncalves | |
| 2005/0099624 A1 * | 5/2005 | Staehr et al. | 356/319 |

FOREIGN PATENT DOCUMENTS

| | | |
|---|---|---|
| EP | 192200 | 8/1986 |
| EP | 383912 | 8/1990 |
| EP | 404258 | 12/1990 |
| EP | 426967 | 5/1991 |
| EP | 1545659 | 6/2005 |
| GB | 2049165 | 12/1980 |
| WO | 9631764 | 10/1996 |
| WO | 0033039 | 6/2000 |
| WO | 0145774 | 6/2001 |
| WO | 02081011 | 10/2002 |

* cited by examiner

Primary Examiner — Nicholas Lucchesi
Assistant Examiner — Ian Holloway
(74) Attorney, Agent, or Firm — Clark Hill PLC

(57) ABSTRACT

The present invention relates to a syringe (1) for use in spectroscopy to identify drugs within the syringe (8). The syringe comprises a optical window section (8) either integral with or attached to the syringe (1). The optical window section (8) has predetermined physical and optical properties that allows radiation to pass through in a known manner to facilitate spectroscopy.

11 Claims, 16 Drawing Sheets

SYRINGE

RELATED/PRIORITY APPLICATION

This application claims priority with respect to New Zealand Patent Application No. 543876, filed on Nov. 29, 2005.

FIELD OF THE INVENTION

This invention relates to liquid drug delivery devices which prevent or minimise adverse drug advents and in particular though not solely to syringes adapted for allowing qualitative and/or quantitative monitoring of their contents.

BACKGROUND TO THE INVENTION

Adverse drug events (ADEs) which are caused by the administration to a patient of intravenous medications of incorrect types, concentrations or dosages may cause irreparable damage or even death in a patient. These types of ADE are entirely preventable and attempts have been made to minimise or avoid their occurrence. An example ADE prevention system is disclosed in U.S. Pat. No. 6,847,899B. In this document plastic tubing forming part of an IV administration set between an IV bag containing a drug to be administered and a needle in a patient's arm is passed through a spectroscopic analyser. The analyser is capable of determining both the type of drug present in the tubing and its concentration. A comparison may be made with expected results from the intended drug type and concentration and a decision made on whether to allow an infusion to continue.

In the above described system, variation in the positioning of the tubing within the spectroscopic analyser and variation in the physical and optical properties of the tubing itself will affect the outcome of the analysis. Furthermore, an IV administration set is often used to transport more than one type of drug, at different times, to the patient. Contamination of the tubing with multiple drug types reduces the ability of the spectroscopic analyser to determine the type of drug currently present.

SUMMARY OF THE INVENTION

Accordingly, it is an object of the present invention to provide a liquid delivery device and/or a docking station for a liquid delivery device which will go at least some way towards overcoming the above disadvantages or which will at least provide the industry with a useful choice.

In one aspect the present invention may be said to consist in a liquid delivery device adapted to deliver a liquid drug to a patient or animal comprising: a reservoir adapted to contain liquid drug to be delivered, the reservoir having an outlet through which liquid drug may be dispensed, a liquid dispensing which causes a movement of the liquid drug from the reservoir to and out of the outlet, wherein the reservoir comprises an optical window section having predetermined optical and physical properties that allows radiation to pass therethrough in a known manner into the interior of the reservoir and that allows radiation affected by the content of the reservoir to pass through as the affected radiation leaves the interior of the reservoir.

Preferably the predetermined optical properties comprise optical density and clarity.

Preferably the predetermined physical properties comprise the thickness and slope and curvature of the reservoir wall in the optical window section.

Preferably the optical window section is provided adjacent to the outlet.

Preferably the optical window section comprises the outlet.

Preferably the reservoir is substantially cylindrical and the optical window section caps the reservoir and comprises the outlet.

Preferably the optical window section is formed separately from the remainder of the reservoir and is attached and sealed thereto in a separate process.

Preferably the optical window section is formed as part of the reservoir in a single process.

Preferably the optical window section is formed from a material which is different from the material from which the remainder of the reservoir is formed.

Preferably the optical window section comprises a transition portion between the reservoir and the outlet wherein the outlet has a smaller diameter than the diameter of the reservoir and wherein the optical window is provided in the transition portion.

Preferably the optical window section comprises at least one planar panel that is at least partially transparent to radiation.

Preferably the optical window section comprises at least four planar panels that are at least partially transparent to radiation.

Preferably the device is adapted to engage in a docking station, the docking station comprising a receptacle adapted to receive the optical window section wherein the at least one planar panel is adapted to be received in the receptacle against a corresponding wall of the receptacle, the corresponding wall preventing rotation of the optical window section received within the receptacle.

Preferably the docking station comprises an optical input for transmitting incident radiation to at least one of the planar panels of the optical window section received in the receptacle, and an optical output for transmitting radiation received from at least one of the planar panels of the optical window section received in the receptacle.

Preferably the optical window section comprises a protrusion for engaging with a corresponding recess in the receptacle to prevent rotation of the optical window section when received in the receptacle.

Preferably the device further comprises optically readable markings on the liquid dispenser and an optical reader with one or more optical detectors arranged to detect the optically readable markings, wherein the optical reader comprises a processor that receives one or more signals from the one or mote optical detectors and generates position data indicating a position of the liquid dispenser relative to the reservoir.

Preferably the processor generates quantity data indicating a quantity of the liquid drug in the reservoir.

Preferably optical reader comprises a transmitter adapted to wirelessly transmit the quantity data or position data to a system.

Preferably the optical reader further comprises an energy storage device for powering the optical reader, the energy storage device coupled to an inductive device, the inductive device adapted to inductively couple to an inductive recharging device to receive energy for recharging the energy storage device.

In another aspect the present invention may be said to consist in a liquid delivery device adapted to deliver a liquid drug to a patient or animal comprising: a reservoir adapted to contain liquid drug to be delivered, the reservoir having an outlet through which liquid drug may be dispensed, a liquid dispenser that causes a movement of the liquid drug from the reservoir to and out of the outlet, and an optical window section having predetermined optical and physical properties that allows radiation to pass therethrough in a known manner into an interior of the optical window section, and that allows radiation affected by a content of the reservoir to pass through as the affected radiation leaves the interior of the window, wherein the optical window section is attached to the reservoir such that the interior of the optical window section is in fluid communication with the reservoir via the outlet, such that liquid within the reservoir can be expelled into the interior of the optical window section.

Preferably the predetermined optical properties comprise optical density and clarity.

Preferably the physical properties comprise the thickness and slope and curvature of a reservoir wall in the optical window section.

Preferably the optical window section is formed from a material which is different from the material from which the reservoir is formed.

Preferably the optical window section comprises at least one planar panel that is at least partially transparent to radiation.

Preferably the optical window section comprises at least four planar panels that are at least partially transparent to radiation.

Preferably the device is adapted to engage in a docking station, the docking station comprising a receptacle adapted to receive the optical window section wherein the at least one planar panel is adapted to be received in the receptacle against a corresponding wall of the receptacle, the corresponding wall preventing rotation of the optical window section received within the receptacle.

Preferably the docking station comprises an optical input for transmitting incident radiation to at least one of the planar panels of the optical window section received in the receptacle, and an optical output for transmitting radiation received from at least one of the planar panels of the optical window section received in the receptacle.

Preferably the optical window section comprises a protrusion for engaging with a corresponding recess in the receptacle to prevent rotation of the optical window when received in the receptacle.

Preferably the device further comprises optically readable markings on the liquid dispenser and an optical reader with at least one optical detector arranged to detect the optically readable markings, wherein the optical reader comprises a processor that receives one or more signals from the one or more optical detectors and generates position data indicating the position of the liquid dispenser relative to the reservoir.

Preferably wherein the processor generates quantity data indicating a quantity of the liquid drug in the reservoir.

Preferably the optical reader comprises a transmitter adapted to wirelessly transmit the quantity data or position data to a system.

Preferably the optical reader further comprises an energy storage device for powering the optical reader, the energy storage device coupled to an inductive device, the inductive device adapted to inductively couple to an inductive recharging device to receive energy for recharging the energy storage device.

In another aspect the present invention may be said to consist in an optical window section for attachment to a liquid delivery device wherein the optical window section has predetermined optical and physical properties that allows radiation to pass therethrough in a known manner into an interior of the optical window section and that allows radiation affected by a content of the optical window section to pass through as the affected radiation leaves the interior of the window.

In another aspect the present invention may be said to consist in a liquid delivery device adapted to deliver a liquid drug to a patient or animal comprising: a reservoir adapted to contain liquid drug to be delivered, the reservoir having an outlet through which liquid drug may be dispensed, a liquid dispenser which causes a movement of the liquid drug from the reservoir to and out of the outlet, and an optical window section coupled to the reservoir, the optical window section having predetermined optical and physical properties that allows radiation to pass therethrough in a known manner into an interior of the optical window section and that allows radiation affected by a content of the reservoir to pass through as the affected radiation leaves the interior of the optical window section, wherein the optical window section comprises at least one planar panel that is at least partially transparent to radiation.

Preferably the optical window section comprises at least four planar panels that are at least partially transparent to radiation.

Preferably the device is adapted to engage in a docking station, the docking station comprising a receptacle adapted to receive the optical window section wherein the at least one planar panel is adapted to be received in the receptacle against a corresponding wall of the receptacle, the corresponding wall preventing rotation of the optical window section received within the receptacle.

Preferably the docking station comprises an optical input for transmitting incident radiation to at least one of the planar panels of the optical window section received in the receptacle, and an optical output for transmitting radiation received from at least one of the planar panels of an optical window section received in a receptacle.

Preferably the optical window section comprises a protrusion for engaging with a corresponding recess in the receptacle to prevent rotation of the optical window when received in the receptacle.

Preferably the device further comprises optically readable markings on the liquid dispenser and an optical reader with at least one optical detector for detecting the optically readable markings, wherein the optical reader comprises a processor that receives one or more signals from the one or more optical detectors and generates position data indicating a position of the liquid dispenser relative to the reservoir.

Preferably the processor generates quantity data indicating a quantity of the liquid drug in the reservoir.

Preferably the optical reader comprises a transmitter adapted to wirelessly transmit the quantity data or position data to a system.

Preferably the optical reader further comprises an energy storage device coupled to an inductive device, the inductive device adapted to inductively couple to an inductive recharging device to receive energy for recharging the energy storage device.

In another aspect the present invention may be said to consist in a docking station adapted to receive a liquid delivery device adapted to deliver a liquid drug to a patient or animal, the liquid delivery device comprising: a reservoir adapted to contain the liquid drug to be delivered, the reservoir having an outlet through which liquid drug may be dispensed, a liquid dispenser which causes a movement of the liquid drug from the reservoir to and out of the outlet, and an optical window section having predetermined optical and physical properties that allows radiation to pass therethrough in a known manner into an interior of the optical window section and that allows radiation affected by a content of the optical window section to pass through as the affected radiation leaves the interior of the optical window section, wherein the optical window section comprises at least one planar panel, and wherein the docking station comprises: a receptacle adapted to receive the optical window section of a liquid delivery device wherein the at least one planar panel of the optical window section is adapted to be received in the receptacle against a corresponding wall of the receptacle, the corresponding wall preventing rotation of the optical window section received within the receptacle.

In another aspect the present invention may be said to consist in a spectroscopic liquid analysis system comprising: a liquid delivery device having a reservoir adapted to contain a liquid drug to be delivered and an outlet through which the liquid drug may be dispensed, and a liquid dispenser which causes movement of the liquid from the reservoir to and out of the outlet, a radiation source that generates radiation that is then directed at a content of the reservoir, and a spectroscopic analyser configured to receive radiation affected by the content of the reservoir and to provide an indication of the composition of the content of the reservoir based upon a spectrum of the received radiation.

Preferably the reservoir comprises an optical window section having predetermined optical and physical properties that allows radiation to pass therethrough in a known manner into an interior of the reservoir and that allows radiation affected by a content of the reservoir to pass through as the affected radiation leaves the interior of the reservoir.

Preferably the liquid delivery device comprises an optical window section coupled to the reservoir having predetermined optical and physical properties that allows radiation to pass therethrough in a known manner into an interior of the optical window section and that allows radiation affected by a content of the optical window section to pass through as the affected radiation leaves the interior of the optical window section.

Preferably the liquid delivery device comprises a syringe.

Preferably the system further comprises a docking station adapted to receive the reservoir in the vicinity of the optical window section.

Preferably the reservoir is substantially cylindrical and the docking station comprises a substantially cylindrical sleeve having a larger internal diameter than the external diameter of the reservoir.

Preferably one opening in die sleeve is smaller than the external diameter of the reservoir.

Preferably the radiation source transmits radiation through an optical window in the docking station aligned in use with the optical window section of the reservoir.

Preferably the radiation source transmits radiation directly at the optical window section of the reservoir without first passing through the docking station.

Preferably the system further comprises a docking station wherein the docking station comprises a receptacle adapted to receive an optical window section of the liquid delivery device wherein the optical window section is formed from at least one planar panel that is at least partially transparent to radiation and wherein the at least one planar panel of the optical window section is adapted to be received in the receptacle against a corresponding wall of the receptacle, the corresponding wall preventing rotation of the optical window section.

Preferably the radiation source produces electromagnetic radiation which is transmitted to the docking station via an optical fibre and electromagnetic radiation affected by the contents of the reservoir is transmitted to the spectroscopic analyser by a further optical fibre.

Preferably the optical fibres are terminated on the docking station and are directed at the optical window section.

Preferably the reservoir is manufactured from a non-metallic material and has provided thereon at least two separated conductive sections, and a further comprising means for obtaining an indication of the capacitance or inductive coupling between the two conductive sections that thereby provide an indication of the amount of liquid in the reservoir.

Preferably the system further comprises optically readable markings on the liquid dispenser and an optical reader with at least one optical detector for detecting the optically readable markings, wherein the optical reader comprises a processor that receives one or mote signals from the one or more optical detectors and generates position data indicating a position of the liquid dispenser relative to the reservoir.

Preferably the processor generates quantity data indicating a quantity of liquid in the reservoir.

Preferably the optical reader comprises a transmitter adapted to wirelessly transmit the quantity data or position data to a system.

Preferably the optical reader further comprises an energy storage device coupled to an inductive device, the inductive device adapted to inductively couple to an inductive recharging device to receive energy for recharging the energy storage device. In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". Related terms such as "comprise" and "comprised" are to be interpreted in the same manner.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

DETAILED DESCRIPTION OF PREFERRED EMBODIMENTS

First Embodiment

Figure 1:
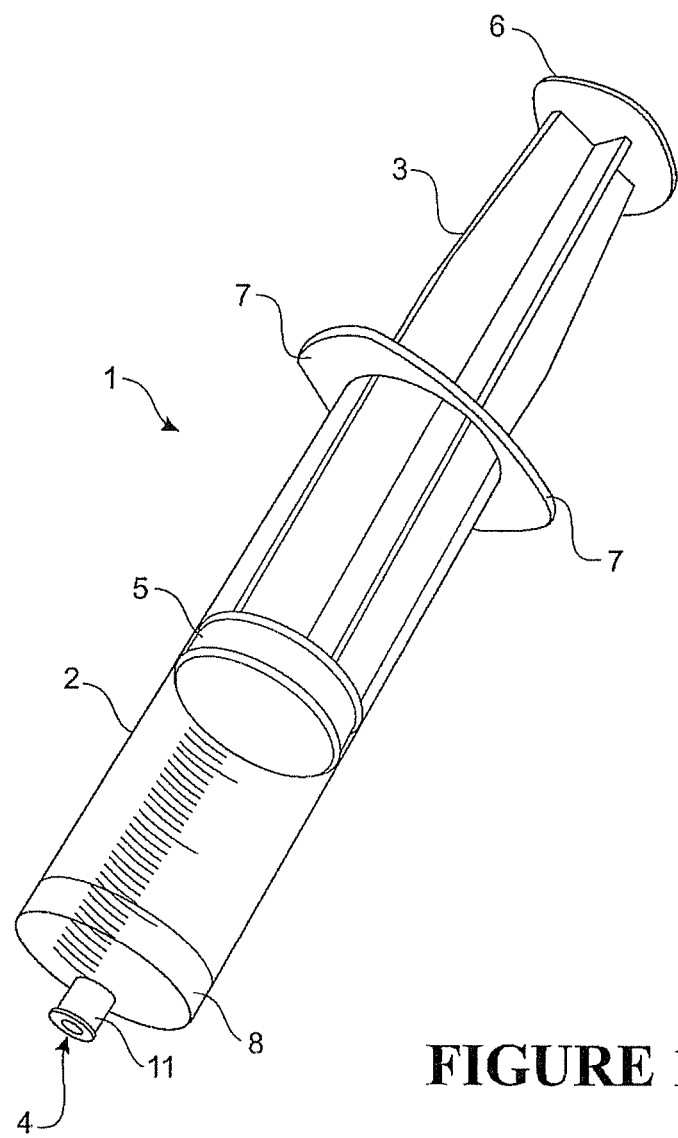
FIG. 1 is a perspective view of a syringe in accordance with a first embodiment of the invention.

With reference to the drawings and in particular FIG. 1, a syringe 1 is shown having a reservoir portion 2 and a liquid dispenser or liquid dispensing means, such as a plunger 3. Although the invention is being described with reference to a syringe it should be noted that the invention is equally applicable to other types of liquid delivery devices which includes a piston and cylinder arrangement such as animal drench guns or oral dosing systems for animal use.

The syringe's plunger 3 slides within the reservoir 2 as a piston slides within a cylinder, to evacuate the contents of the reservoir through an outlet 4. The outlet may be provided with a needle fitting (not shown) for intravenous delivery of the content of the reservoir to a patient. Alternatively, as shown, an outlet fitting 11 such as a well known "luer lock" or "luer slip" fitting may be provided at the outlet of the reservoir. These fittings allow for twist lock or press fit engagement with a complimentary fitting on an inlet of a luer forming part of in IV administration set connected to an indwelling vein access device (such as a needle or cannula) inserted in a patient. Alternatively, the luer may simply be connected by tubing to a patient's indwelling vein access device (not shown).

As is well known, plunger 3 is provided with a rubber or elastomeric head 5 which is a tight fit within the substantially cylindrically shaped reservoir 2 and which forms a seal with the inner wall thereof. The end of plunger 3 furthest from the reservoir is provided with a flange 6 adapted to be pressed by a user's thumb whilst the user's first and second fingers are positioned beneath a flange 7 at the open end of reservoir 2. In use, as is well known, a user presses flange 6 with his or her thumb whilst pulling flange 7 with the first and second fingers to cause liquid within the reservoir to be dispensed from outlet 4. The syringe may be pre-loaded with liquid or can be filled via the outlet 4 in the known way.

Reservoir 2 is preferably transparent or translucent so that a user is able to determine the amount of liquid, such as a liquid drug, held therein. Reservoir 2 may be formed from a medical grade plastics or glass material such as HDPE for example. Reservoir 2 includes an optical window section 8 which is preferably formed from a different material to the remainder of the reservoir 2. The material from which the optical window section 8 is manufactured is a high quality plastics or glass with close manufacturing tolerances for both its physical and optical properties. Suitable exemplary materials from which the optical window may be made include cast or extruded Acrylic plastics, Polycarbonate plastics (such as LEXAN® manufactured by GE Plastics), Butyrate plastics, polypropylene and Clear PVC.

In terms of the controlled physical properties, one or more of the thickness, slope and curvature of the optical window section should be within predetermined ranges. The material chosen for the optical window should have low distortion properties, no or minimal fading, shrinking lines or optical distortion. Flatness is also important as is the ability to reproduce wall thickness and, for use in a transmission mode spectroscopic system, wall separation. The wall thickness may range from about 0.6 mm to about 1.2 mm and could be 1 mm. The wall separation (the distance between the wall surface through which light enters and the surface where affected light enters the sensor opposite) may range from about 8 mm to about 12 mm, and preferably around 10 mm. Preferably, the predetermined optical characteristics include the optical density and clarity of the optical window section. Importantly, the material chosen for the optical window should be substantially transparent with low absorbance, preferably a low absorbance particularly in the near infrared range. Polycarbonate plastics may therefore be especially suitable.

Figure 2:
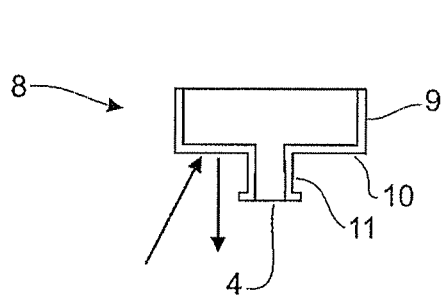
FIG. 2 is a cross-sectional view of the optical window section of the syringe of FIG. 1 showing its use in reflectance mode spectroscopy.
Figure 3:
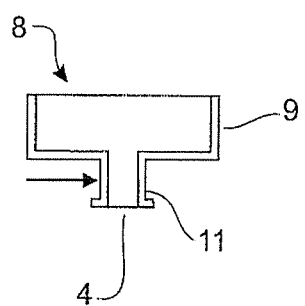
FIG. 3 is a cross-sectional view of the optical window section of the syringe of FIG. 1 showing its use in transmission mode spectroscopy.

The optical window section 8 is shown in more detail in FIGS. 2 and 3 in schematic form. The optical window section includes a substantially cylindrical wall section 9, a transition section 10 and an outlet fitting section 11 in which the outlet 4 is formed. Preferably, the entire optical window section 8 is formed from a single homogeneous material which is connected or bonded or sealed to the remaining, open-ended portion of the reservoir 2 during manufacture of the reservoir.

The syringe according to the present invention is adapted to be used in conjunction with a qualitative analysis device such as a spectroscopic analyser to determine the composition of material within the reservoir 2. Accordingly, optical window section 8 is manufactured within known optical and physical tolerances so that it has a known affect on radiation passing therethrough. The optical window section 8 will therefore cause a known reduction in light intensity at known frequencies and this effect can be factored in to calculations carried out by the spectroscopic analyser. The spectroscopic analyser may then determine an accurate spectroscopic "fingerprint" of the liquid within reservoir 2 for comparison with spectroscopic data of known drugs. In this way, as a drug is being administered to a patient by the syringe or just prior to delivery of a drug using the syringe, it is possible to check that the drug being delivered is that which is intended to thereby avoid or reduce the risk of an adverse drug event.

As shown in FIG. 2, reflectance mode spectroscopic analysis may be carried out on the syringe by causing light, for example in the near-infrared (NIR) spectrum, to be incident on the optical window section 8. The incident light will be transmitted through the optical window section while being effected by the optical window section in a known way, interact with the contents within receptacle 2 and then some of the incident light will be reflected back (as shown by the arrows) through the optical window section to a detector having been affected in a known way as it travels back through the optical window section. Incident light is preferably directed at the transition section 10. The piston should not be fully depressed as it may interfere with the light path through the liquid. The minimum clearance between the end of the plunger and the wall of the transition section of the optical window depends upon the choice of plastics or glass material, the width of the light beam, the angles of incidence and reflection and, in the case of a system with a lens, the position of the focal point within the syringe. As an example, the minimum clearance may be less than about 5 mm.

Any suitable method of spectroscopic analysis could be used, for example the system disclosed in our PCT application published as WO 2004/025233A. FTIR (Fourier Transform Infra-Red spectroscopic analysis), Raman scattering, UV/VIS (ultra-violet/visible) and infra-red methods could also be employed. Some modes of magnetic resonance and low power radioactive radiation could also be used to determine the composition of the liquid within the receptacle.

Alternatively, as shown in FIG. 3, transmission mode spectroscopy could be employed to determine the composition of the contents of the reservoir. For example, as shown in FIG. 3, radiation such as light from a radiation source may be directed through the luer fitting 11, the walls of which will have a known affect on the transmission of the radiation both into and out of the optical window section.

Although not shown, outlet 4 may include a valve to retain liquid in the receptacle until plunger 3 is pushed. The diameter and roundness of the substantially cylindrical outlet fitting section 11 is also manufactured to strict tolerances and therefore the path length of the radiation travelling through the contents of the reservoir is accurately known which is of course essential for transmission mode spectroscopic analysis. In this way, measurements are made repeatable so that useful comparisons and/or calibration can be performed. Alternatively, the substantially cylindrical outlet fitting section 11 could be provided with one or more flat sides or could be square or rectangular in cross-section. This may however require additional means to orient the syringe within housing 12 to ensure that the incident light beam is directed substantially normal to a flattened face of the outlet fitting.

Figure 4:
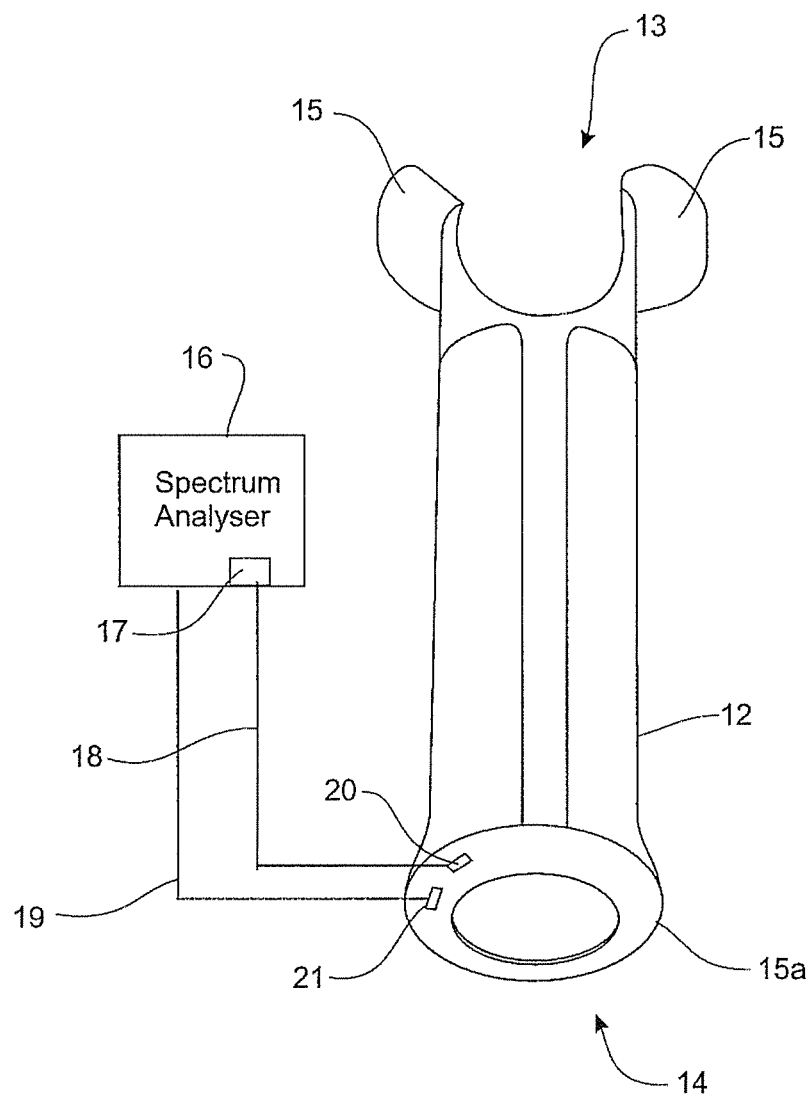
FIG. 4 is a perspective view of a docking station or sleeve adapted to receive the syringe of FIG. 1 in order to allow spectroscopic analysis on the contents of the syringe to occur.

FIG. 4 shows a housing 12 adapted to receive syringe 1 to enable spectroscopic analysis of the syringe's contents to be carried out. Housing 12 forms a substantially cylindrical docking station or holder for the syringe. Housing 12 has an open first end 13 adapted to receive the reservoir 2 and a second open end 14 having a smaller opening through which outlet fitting 11 may, in use, protrude. Flanges 15 at the first end of the housing form a seat for reservoir flanges 7 when the reservoir is positioned appropriately within the housing. A annular conical ring section 15a forms an optical window in the holder which, in use, is aligned with the transition section 10 of the reservoir's optical window 8. The physical and optical properties of at least the housing's optical window section are specified and controlled during manufacture in a similar manner to the properties of optical window section 8 of reservoir 2.

To enable the combination liquid delivery device (or syringe) and housing according to the invention to remain as compact and lightweight and as possible, it is preferred that the spectroscopic analyser is positioned remotely. Accordingly, the spectroscopic analyser 16 including radiation source 17 shown in FIG. 4 is connected to housing 12 by optical fibres 18 and 19 having terminations 20 and 21 respectively on the housing. Terminations 20 and 21 ensure that the ends of the fibres are coupled to the optical window 15a of the housing to receive or transmit radiation in appropriate directions. As an example, the incident and reflected beams may have an angle of about 30° between them.

Dependent upon the type of radiation used, other transmission mediums could be used. Alternatively, the radiation source, such as a light emitting diode (LED) could be mounted on the housing and controlled via a wired or wireless connection to the spectrum analyser.

Figure 5:
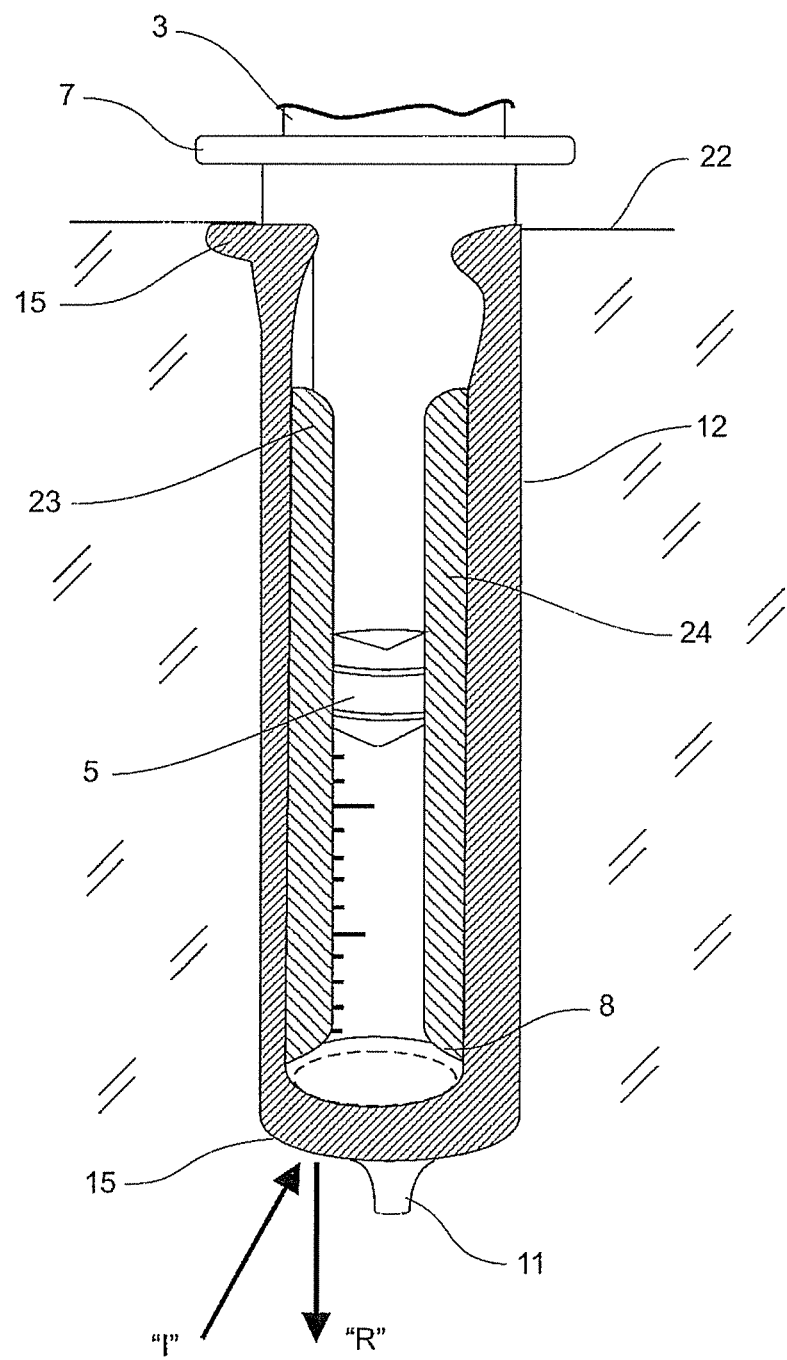
FIG. 5 is a side elevation of the syringe of FIG. 1 within the docking station of FIG. 4.

As shown in FIG. 5, housing 12 could be built into a tray or cabinet or other larger fixture. In this case, the spectrum analyser may also be built into that larger fixture. Furthermore, rather than requiring optical fibres to connect the housing to the spectroscopic analyser, light beams with any necessary lens system could be transmitted through an air path to and/or from the reservoir.

FIG. 5 also shows a further aspect of the invention wherein the syringe is capable of quantitative analysis of the syringe's contents. This may be in conjunction with the spectroscopic qualitative analysis described above or may be independent thereof. The quantitative analysis is provided by electrically conductive segments 23 and 24 on reservoir 2. In the example shown where the liquid delivery device constitutes a syringe, conductive segments 23 and 24 may be located substantially on opposite sides of the longitudinal axis of the reservoir extending axially substantially the entire length (or a substantial portion thereof) of the reservoir. The conductive segments may be formed as electrodes from a layer of conductive foil such as aluminum or copper. Alternatively, the conductive layers may be formed from a conductive plastics material or a plastics material that is doped with a conductive agent such as graphite or a metallic compound.

The two conductive electrodes form the plates of a capacitor. The dielectric constant of the material from which the wall(s) of the reservoir are formed or air is significantly different to the dielectric constant of the (often water-based) liquid drugs inside the reservoir of the syringe. As an example, a conventional 10 mL disposable plastics syringe will change capacitance from a few picofarads to tens of picofarads from empty to full of a water-based drug. These amounts obviously depend upon the size of the electrodes and the dimensions of the syringe.

Displacement of plunger 3 within reservoir 2 causes liquid within the reservoir to exit via outlet 4. The capacitance of the capacitor formed by the electrodes and air/liquid/plastics material therebetween to vary as a result. It has been found that the capacitance of the capacitor varies substantially proportionally to the amount of fluid remaining inside the reservoir. By carrying out experiments with various different liquid drugs, it is possible to develop mathematical relationships or a lookup table relating capacitance (or an indicator thereof) and the amount of fluid in the reservoir. Therefore, by simply determining the capacitance of the capacitor formed by the electrodes printed or applied to the surface or within the wall of the reservoir, it is possible to calculate the amount of fluid remaining in the reservoir. During a continuous time measurement when liquid is being evacuated from the reservoir, the flow rate of the liquid can easily be calculated.

In an alternative (or in addition) to electrodes forming the electrically conductive segments 23 and 24, coils could be provided on either side of the reservoir. The coils could be etched onto the sides of the reservoir or could be provided on adhesive labels for example. It has been found that the inductive coupling (or mutual inductance) between the two coils is substantially directly proportional to the amount of liquid remaining in the reservoir.

In either the capacitive or inductive situations, the beat frequency or phase shift of a tuned circuit may be used to determine the capacitance or inductive coupling between the conductive sections. An electronic circuit providing a high frequency oscillating voltage or current to an LC resonant tank circuit including the reservoir capacitor or inductors could be tuned to a particular resonant frequency when the reservoir is empty. The tuned circuit will be de-tuned as a result of the liquid within the reservoir and this change in resonant frequency can be detected and used to calculate capacitance or inductive coupling. The frequency or phase shift caused by the change may also be directly proportional to the amount of liquid between the capacitor plates or coils. The effect of the liquid on radio frequency transmission from an aerial positioned on the wall of the reservoir could also be used to achieve the same effect. In the case of a capacitive circuit, the electronic detector circuit may include a circuit that is tuned to detect the charge and/or discharge of an external capacitor formed by the capacitor plates and the liquid. A regular pulse train of current in the form of a square wave (of less than 100 kHz for example) may be supplied to the capacitor and the charge and/or discharge time of the unknown capacitor used as an indicator of, or to determine its, capacitance. Alternatively, a comparator circuit could determine the time taken for the voltage across the unknown capacitor to reach a predetermined value and this could provide an indication of capacitance.

The conductive sections 23 and 24, whether electrodes or coils, require conductive terminations which could be provided near the top of reservoir 2. The conductive terminations are connected to an electronic circuit capable of determining capacitance or inductive coupling or an indication thereof or changes in one of these parameters. Alternatively, raw detected values could be transmitted to a remote device at which analysis to determine capacitance or inductive coupling or an indication of one of these parameters is conducted. The electronic circuit may include an electronic controller executing software which inputs an indication of capacitance or inductive coupling via an analogue to digital converter, analogue comparator or pulse sensing logic circuit for example. The electronic circuit could conveniently be mounted on or to syringe 1 or housing 12 with connections to the conductive terminations.

Figure 6:
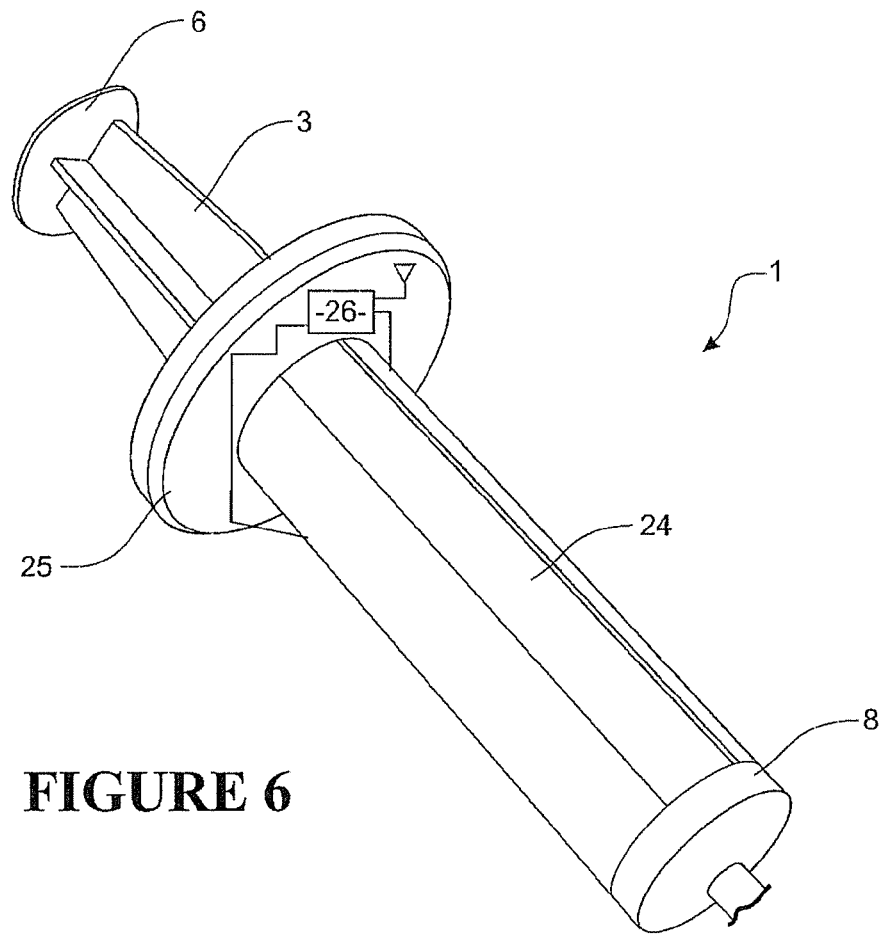
FIG. 6 is a perspective view of a syringe which also includes a mechanism for determining the amount of liquid within the syringe.

Alternatively, as shown in FIG. 6, a separate housing or sleeve 25 may be provided about reservoir 2 which houses the electronic sensing circuit 26 (shown schematically) and includes contacts which mate with the electrical terminations on the surface of reservoir 2 (circuit 26 is shown connected to conductor section 24 only as conductor section 23 is hidden from view). Note that sleeve 25 has not been shown in FIG. 5 for clarity purposes only. Sleeve 25 may require a power source such as a small battery and would preferably include a transmitter (and optionally a receiver or transceiver) to allow short range transmission of radio frequency signals (using the Bluetooth® protocol for example). Sleeve 25 may be formed as a ring or torus for example which has an internal diameter which is a sliding fit about reservoir 2. The reservoir 2 of the syringe could then be slid into the ring until the ring reaches its operative position with the conductive terminations of the electrical sections 23 and 24 connecting with contacts on the internal surface of the ring. The operative position may correspond with sleeve 25 contacting flange 7 of the reservoir so that the user may use sleeve 25 as finger supports rather than flange 7 during use of the syringe. Once in the operative position, the sleeve may simply remain there through a tight fit or could be bonded or welded into place.

Alternatively, rather than being subsequently mounted to the syringe, sleeve 25 may be formed integrally with the reservoir.

The electronic circuit within sleeve 25 could also include a memory device such as an EEPROM (Electrically Erasable Programmable Read-Only Memory) for storing data pertinent to the syringe/reservoir and/or the intended content of the syringe. For example, one or more of the following data fields could be stored in the memory device:

a unique identifier for the syringe/reservoir, an identifier of the type of drug intended to be used with the syringe, the capacitance or inductive coupling value associated with the reservoir when empty, the expected capacitance or inductive coupling when the syringe is fully loaded, calibration information or lookup table(s) to allow detected capacitance/inductance data to be accurately transformed into a remaining volume value, and a spectroscopic fingerprint of the expected content of the reservoir for cross-checking purposes (that is, spectrum data for comparing with the output from the spectroscopic analyser to determine whether the composition of syringe's contents is as expected.

Figure 7:
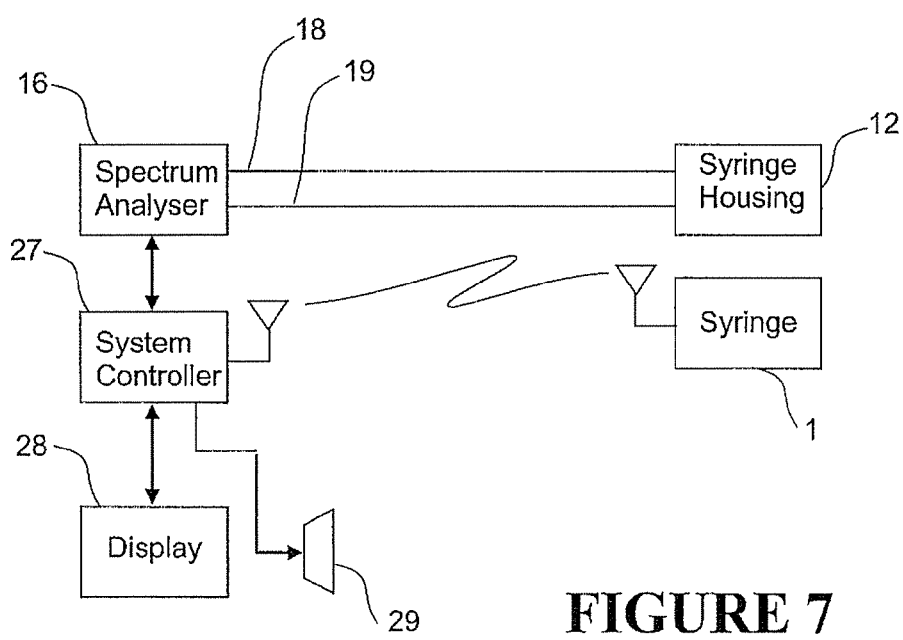
FIG. 7 is a schematic block diagram of a spectroscopic analysis system including the syringe of FIGS. 1 and/or 6.

This data or portions of it along with capacitance or inductive coupling data (or data indicative thereof) could be transmitted to a remote receiving device connected to a system controller 27 as shown in FIG. 7 that executes software instructions. The system controller is connected to the spectroscopic analyser 16 and an output device such as a display 28 unit and/or an audio device such as a speaker 29. System controller 27 receives spectrum data from the spectroscopic analyser and may compare this determined data with stored "fingerprint" data for known liquid drugs to determine a best match drug. The display unit 28 and/or speaker 29 may then provide visual and/or audible information to a user of the drug which most closely matches the contents of the reservoir. Alternatively, the display device 28 could output a graphical display of the drug's photometric spectrum for review by the user.

If memory device within sleeve 25 is provided with data on the expected content of the syringe or a cross-check fingerprint then this data may also be used by the system controller to advise a user whether the detected drug matches the expected drug characteristics according to the data held in the syringe. If sleeve 25 included calibration or empty/full capacitance or inductive coupling data then this could be used in the system controller's calculations to determine the amount of fluid within the reservoir and a visual and/or audible output of this parameter could also be provided to the user.

Second Embodiment

FIGS. 8 to 14 show a second embodiment of the invention, which includes among other things comprises an optical reader for determining the quantity of liquid drug in the syringe and a flat-sided optical window. This embodiment also includes optionally comprises a corresponding docking station. The second embodiment is utilised in a similar manner as the first embodiment. That is, it can be used to implement qualitative and quantitative analysis of the contents of the syringe. Again, while this embodiment is described with reference to a syringe, it should be noted that the invention is equally applicable to other types of liquid delivery devices noted for the first embodiment.

Figure 8:
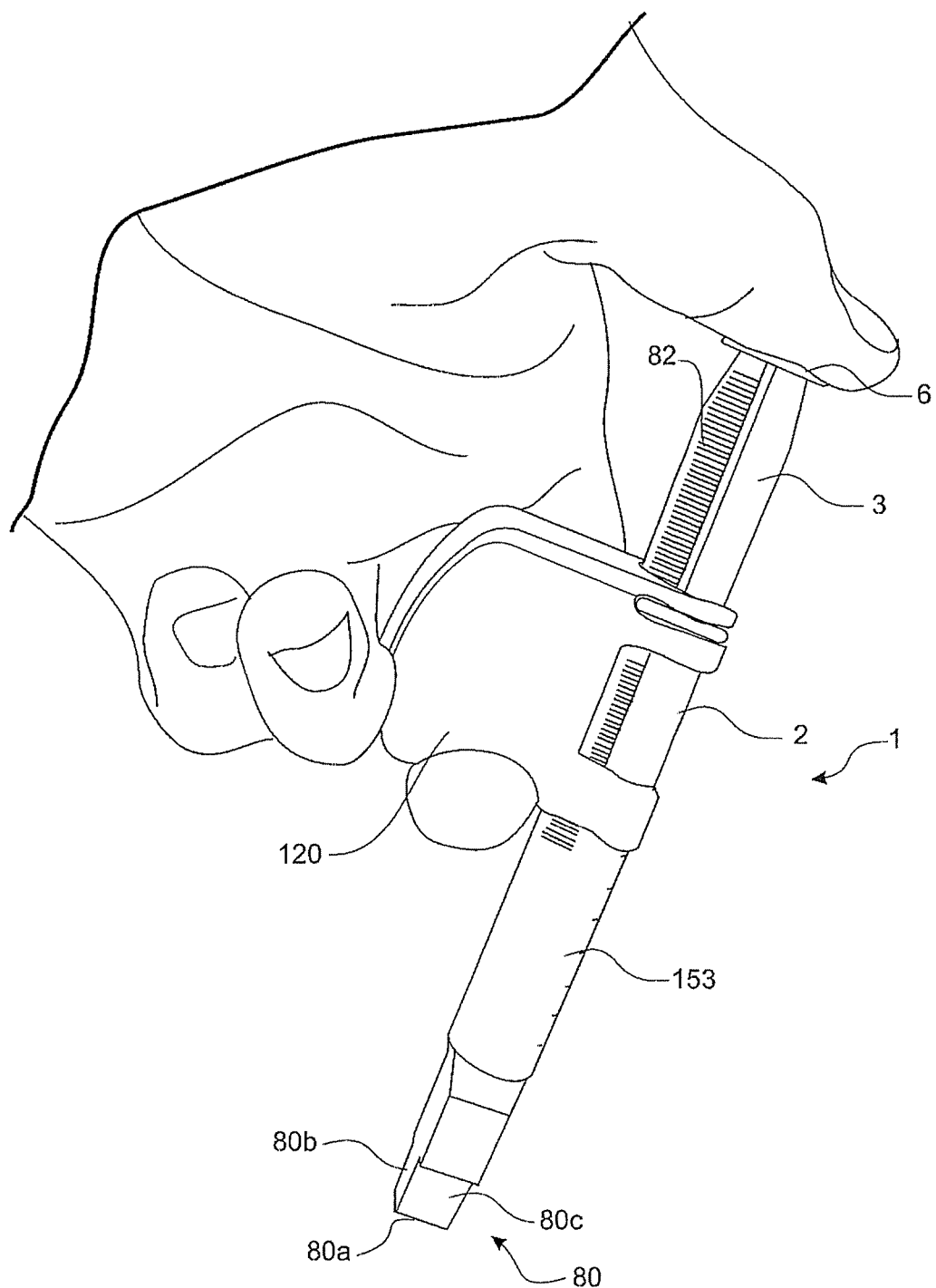
FIG. 8 is a perspective view of a syringe in accordance with a second embodiment of the invention.
Figure 10A:
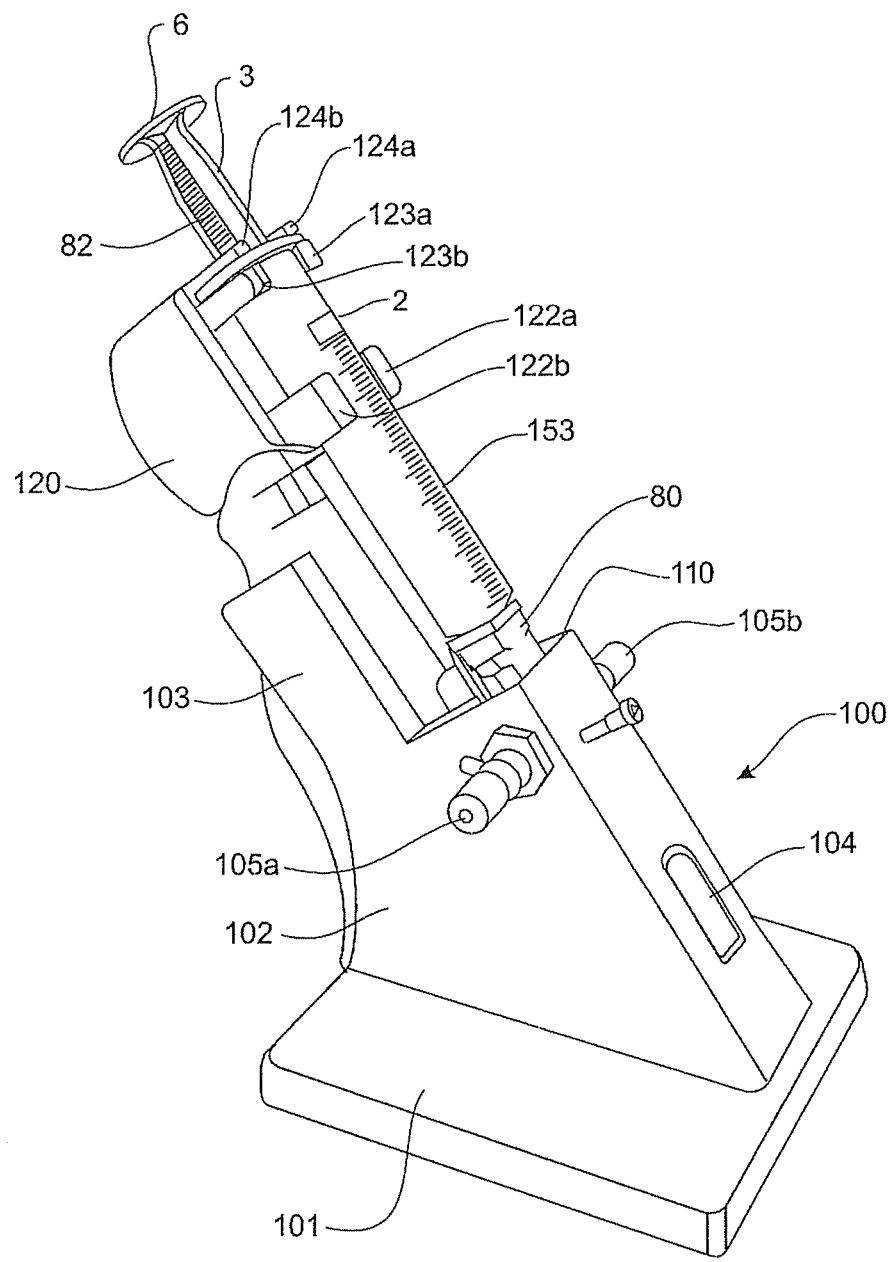
FIGS. 10a-10c are various views of the syringe docked in a docking station.
Figure 10B:
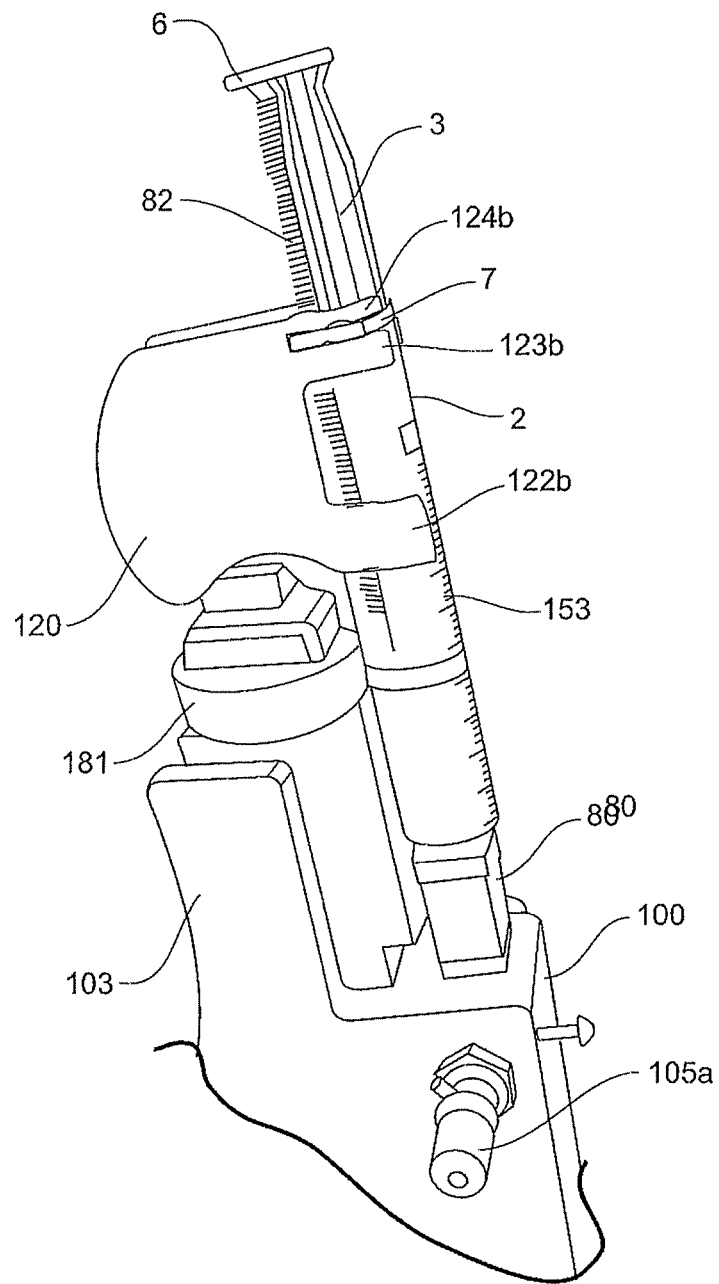
Figure 10C:
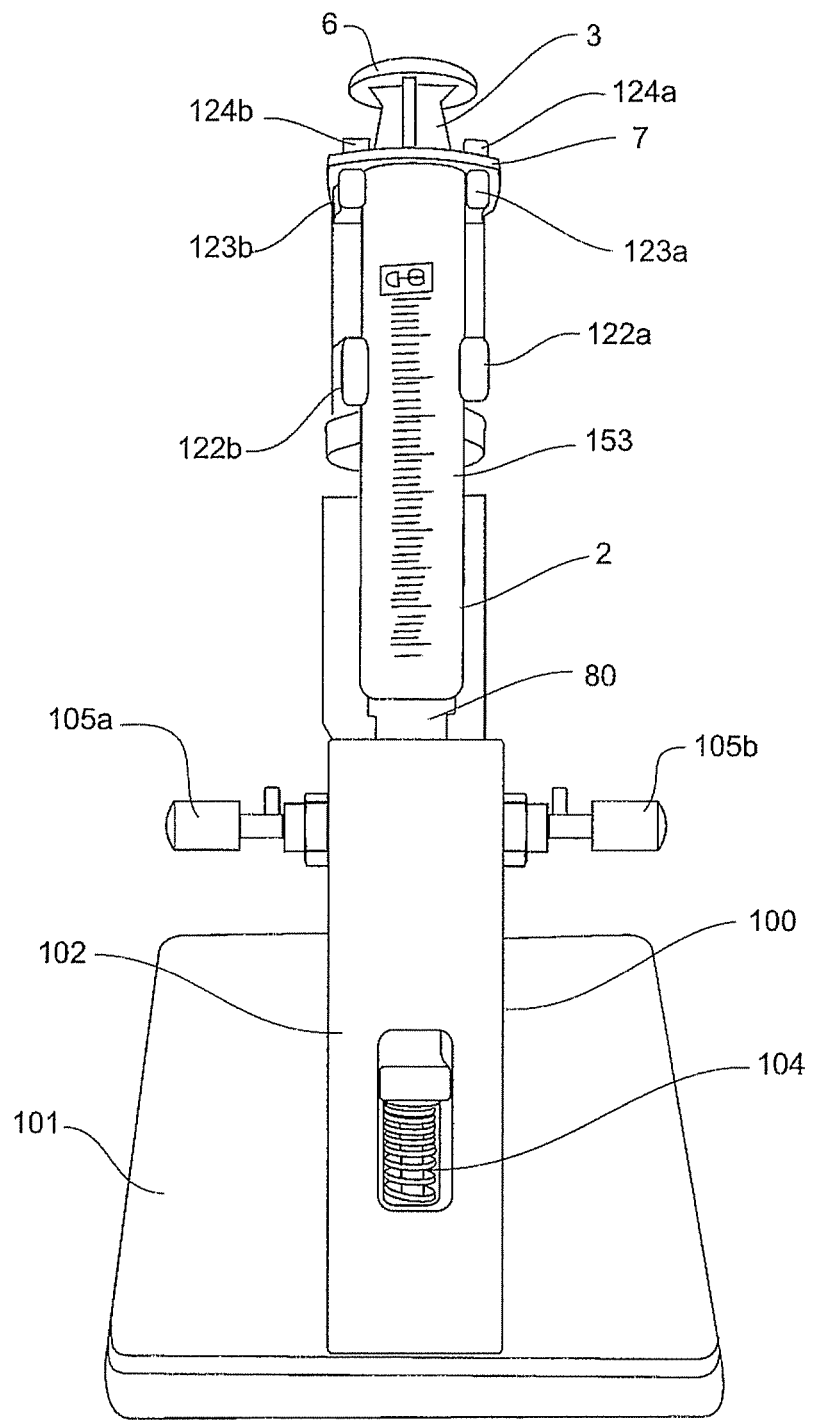

Referring to FIG. 8, the basic syringe 1 is similar to that shown in FIG. 1 and has the same reservoir portion 2 and liquid dispensing means or plunger 3. The general description of the syringe for the first embodiment applies for the second embodiment and the details will not be repeated here. The optical window section 80 in the second embodiment is formed as a flat four-sided transparent portion that attaches to or is integrally formed with the bottom portion of the syringe. The syringe 1 also comprises a detachable optical reader 81120. The optical reader detects markings 82 on the syringe plunger 3 to determine the extent to which the plunger has been moved, and from this, the quantity of liquid in the syringe can be inferred. The reader 120 comprises electronics (to be described later) for reading and processing the optical information, and a transceiver for communication the information to a remote system. The optical reader 120 is also fashioned to function as a handle to assist use of the device. Referring briefly to FIGS. 10*a* to 10*c*, the syringe is adapted to sit in a holder 100. This enables spectral analysis of the contents of the syringe.

The syringe, 1 and in particular the window 80 will be described in more detail with reference to FIG. 8 and the schematic cross-section depiction in FIG. 9*a*. The flat-sided window comprises four planar transparent panels 80*a*-80*d* (of which three are visible in FIG. 8) that allow for transmission of radiation. The panels are arranged at right angles to form a receptacle 91 with a square or rectangular cross-section. The panels may be square or rectangular and need not be all the same size. The receptacle 91 can hold a portion of the liquid in the reservoir and is in fluid communication with it. This enables the device to be used in transmission and reflectance spectral analysis equipment. The bottom portion of the window 80 is substantially closed off (not visible), except for an outlet 94 through which drug expelled from the syringe 1 can escape. The window outlet might also comprise, or be adapted for connection to, a needle 90 or IV administration set (not shown) or other delivery device. The window 80 is formed from a suitable optical material, the panels 80*a*-80*d* being joined by a suitable method or moulded as one piece.

Figure 9C:
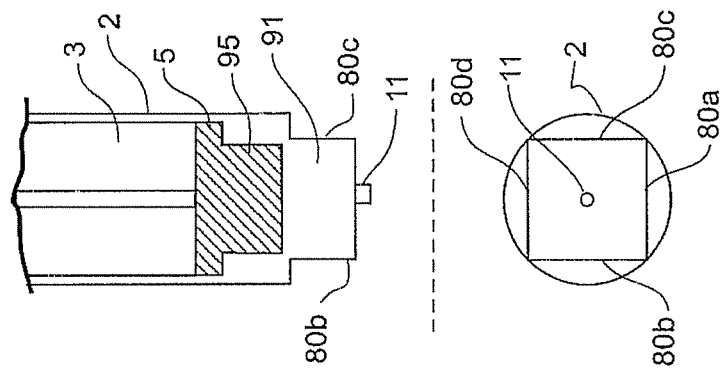
FIGS. 9a, 9b and 9c are plan views of two optical window sections of the second embodiment.
Figure 9B:
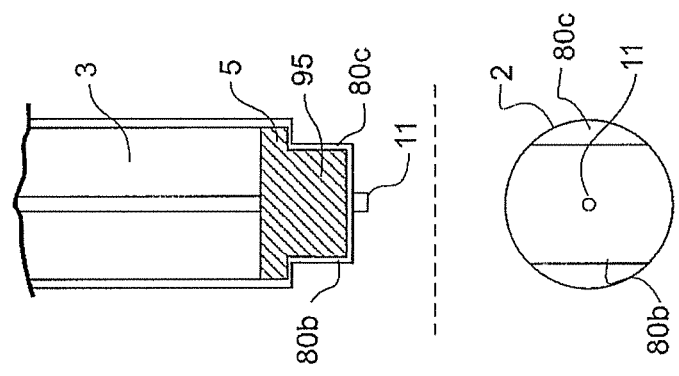
Figure 9A:
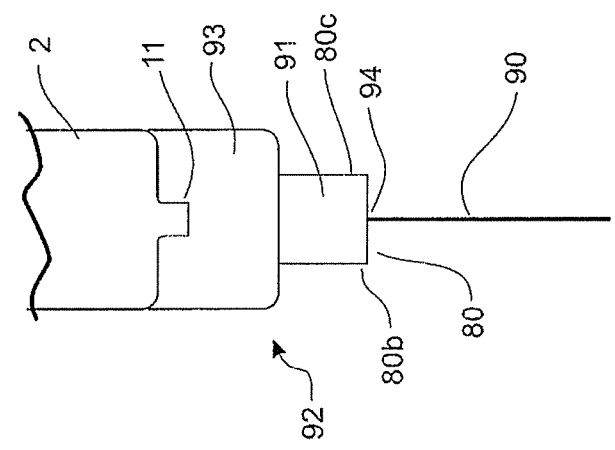

The window 80 of FIGS. 8 and 9*a* is formed as part of a separate component 92 that is attachable to an existing syringe 1 and more particularly the reservoir 2 of the syringe. The component 92 includes a square attachment portion 93 extending from the planar window 80, which has a larger cross-sectional area. The attachment portion 93 is dimensioned to enable the component 92 to sit over the outlet fitting 11 and attach to the bottom of the standard syringe 1 reservoir. The attachment portion 93 will include an engagement means (not visible) that enables the component 92 to connect to the outlet 11 or other part of the syringe bottom 1 to effect a connection thereto. In a possible variation, the attachment portion 92 could be integrally attached to or formed with the syringe 1 reservoir via a suitable moulding or other process. The attachment portion 92 is substantially hollow to allow liquid expelled from the syringe reservoir 2 to pass through to the outlet 94 in the window bottom and escape the syringe 1 via needle 90. Liquid can also be retained in the receptacle 91 of the window 80 for analysis purposes. The component 92 could be produced and supplied independently from the syringe 1, and would be adapted for use with standard issue syringes. Preferably there are four planar panels although less are possible. In an alternative embodiment shown in FIG. 9*b*, there is no attachment portion, but rather the flat-sided window 80 is integrally formed with the syringe 1 bottom during the manufacturing process of the syringe. A luer 11 is formed at the bottom of the window. The window could be manufactured separately and then moulded to a syringe, or moulded as part of the syringe as a single process, such as an injection moulding process. Preferably, the syringe and window could be formed from polypropylene. The advantage of using the same plastic for the syringe body and the window is that the syringe/window can be formed in a single piece as a single process. This is in contrast to where the window might be formed as a separate component of a different plastics, and the welded or otherwise integrated with the syringe body. In this case, the window 80 forms an integral part of the reservoir. The window 80 is effectively formed as part of the syringe 1, with two side panel windows "cut-off" to provide parallel window sections. In another alternative shown in FIG. 9*c* 4four flat panels 80*a*-80*d* are formed as part of the bottom of the syringe reservoir 2.

The flat-sided optical window 80 is formed of a suitable material with close manufacturing tolerances for both its physical and optical properties. Suitable materials from which the optical window may be made comprise cast or extruded Acrylic plastics, Polycarbonate plastics, Butyrate plastics, polypropylene and Clear PVC. The planar nature of each side provides a known path for incident radiation, and the thickness of each transparent side is known to ensure it is suitable for the wavelength radiation being used.

In terms of the controlled physical properties, the thickness of the window panels 80*a*-80*d* should be within predetermined ranges. Preferably, they are 1 mm thick. The material chosen for the optical window should have low distortion properties, no or minimal fading, shrinking lines or optical distortion. Flatness is also important as is the ability to reproduce wall thickness and, for use in a transmission mode spectroscopic system, wall separation. The wall thickness may range from about 0.6 mm to about 1.2 mm and preferably 1 mm thick. The wall separation (the distance between the wall surface through which light enters and the surface where affected light enters the sensor opposite) may range from about 8 mm to about 12 mm, and preferably around 10 mm. Preferably, the predetermined optical characteristics include the optical density and clarity of the optical window section. Importantly, the material chosen for the optical window should be substantially transparent with low absorbance, preferably a low absorbance particularly in the near infra-red range Polycarbonate plastics may therefore be especially suitable.

Referring now to FIGS. 10*a* to 10*c*, the syringe 1 with an attached or integrally formed flat-sided window 80 is adapted for use with a holder or docking station 100. FIG. 10*a* shows a perspective view of a syringe 1 partially installed in the holder 100, and FIG. 10*b* shows in more detail a syringe 1 being installed. FIG. 10*c* shows a plan elevation view of a syringe 1 installed in the holder 100. The holder 100 retains the syringe 1 in place, and enables radiation to be directed towards the window 80 to enable spectral analysis of the syringe 1 contents. The holder comprises a base 101, with a docking stand 102 extending from the base. The stand is preferably angled to assist with convenient operation. The stand 102 comprises a support portion 103 for supporting a syringe 1 installed in the stand. The stand also includes an internal recess 110 (shown in FIG. 11*a*). The recess is shaped and dimensioned to receive the flat-sided window 80 attached to the syringe. Once installed, the window 80 is retained in the recess 110 and the reservoir 2 of the syringe 1 rests against the support 103. The stand further comprises a second internal recess (not visible) extending from the first recess 110 towards the base 101 adapted to receive a needle attached to the window 80. The docking stand 102 might also include a window, aperture or other viewing portion to enable the user to view the docking process. This window shows a spring loaded reference tile 104. When the syringe is not in the docking station, the spring pushes a reference tile into the light path. When the syringe is in the holder, the reference tile is displaced and the sample under investigation can be optically analysed.

The stand 102 has two optical terminations 105*a*, 105*b* positioned on the outer walls of the stand either side of the internal recess 110. Each termination 105*a*, 105*b* is adapted for coupling to a fibre optic cable or other optical transmission means by way of a screw mechanism or similar. Each termination also has an internal aperture 113 or other optical transmission means that extends through the termination and through the exterior wall of the stand adjacent the recess to provide an optical path 111 (e.g. see FIG. 11a) to the recess 110. By coupling a fibre optic cable or the like to a termination 105a, 105b, radiation can be transmitted into the recess 110. When a flat-sided widow 80 is in the recess 110, this radiation 111 will be transferred through the window 80 into the liquid inside. Likewise, radiation 112 coming from the recess can be received at an external sensor coupled to the termination 105a.

Figure 11A:
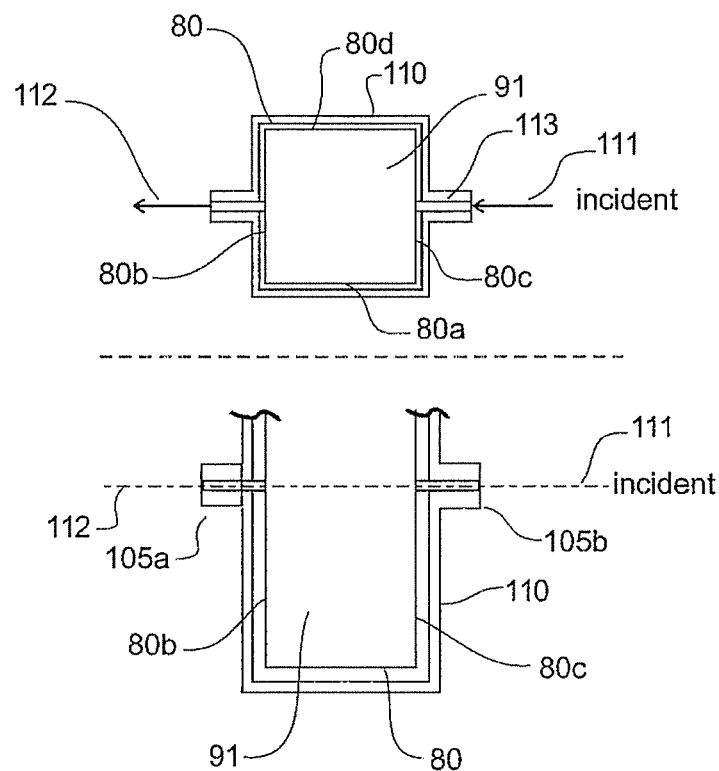
FIGS. 11a, 11b are plan views of the optical window docked in recess of the docking station.

FIG. 11a is a top cross-sectional view showing the flat-sided window 80 of the syringe 1 positioned snugly in the recess 110 of the holder 100. In particular, the tight fit and square shape prevents rotational movement of the syringe. As noted earlier, the window 80 could be formed with a rectangular shaped cross-section. The known properties of the flat-sided window, along with its secure retention to reduce the risk of rotation provides more certainty in the optical parameters. As rotation of the window in the holder is prevented, or at least reduced, the incident radiation path 111 will be known along with the known properties of the window 80, which provides for a more accurate determination of the contents of the liquid drug. Preferably, the incident path 111 of radiation incident on the window panel 80cb from the termination 105b will be normal to the face of the window panel 80cb. Similarly, radiation 112 transmitted through or reflected from liquid in the window 80 will travel normally through the window panel 80bc and to the receiving termination 105a.

Figure 11B:
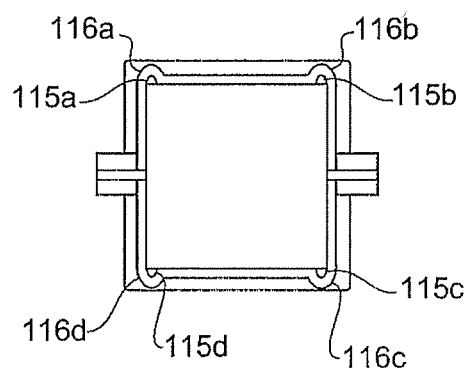

Referring to FIG. 11b, in a further embodiment, the flat-sided optical window 80 might include rails, engagement portions or other protrusions 115a-115d, which engage with a corresponding channel 116a-116d or the like in the holder 100. This further assists in retaining the installed syringe 1 in a fixed rotational position. It also assists with insertion and location of the window 80 into the recess in the correct orientation.

Referring to FIG. 9b, the plunger, which is provided with a rubber or elastomeric head 5, also preferably comprises an extension portion 95. The extension portion is profiled to slide with a tight fit into the window portion 80 when the plunger 6 is pushed downwards as shown in FIG. 9b. This ensures any liquid that resides in the window portion 80 receptacle 91 is expelled through the outlet 94 upon actuating the syringe. While the extension portion 95 is not essential, it prevents wastage of liquid which might remain in the window portion 80 by use of a standard plunger head. FIG. 9c shows the plunger such that the extension is retracted from the receptacle 91.

Figure 12A:
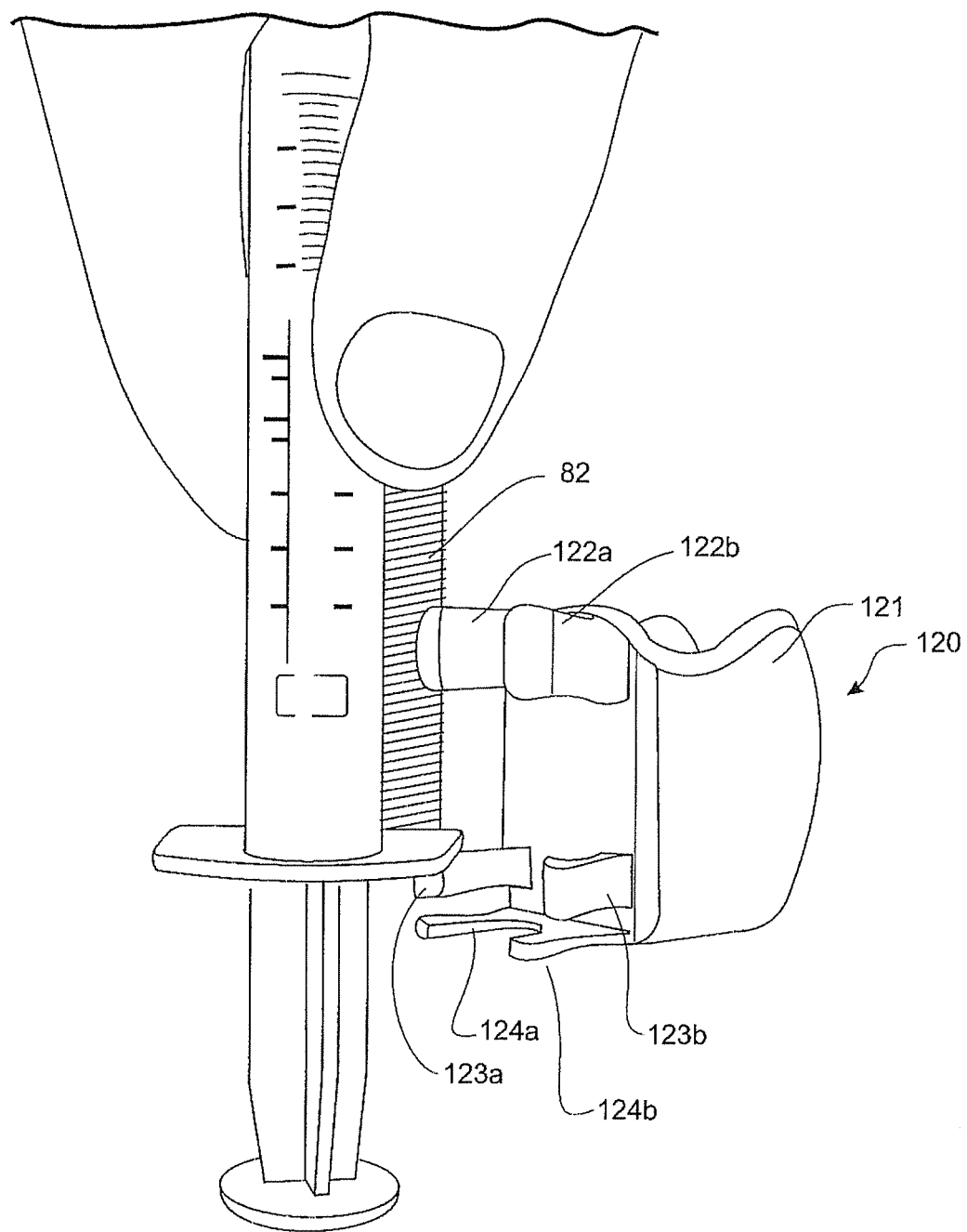
FIGS. 12a, 12b are perspective views of an optical reader adapted for attachment to the syringe.
Figure 12B:
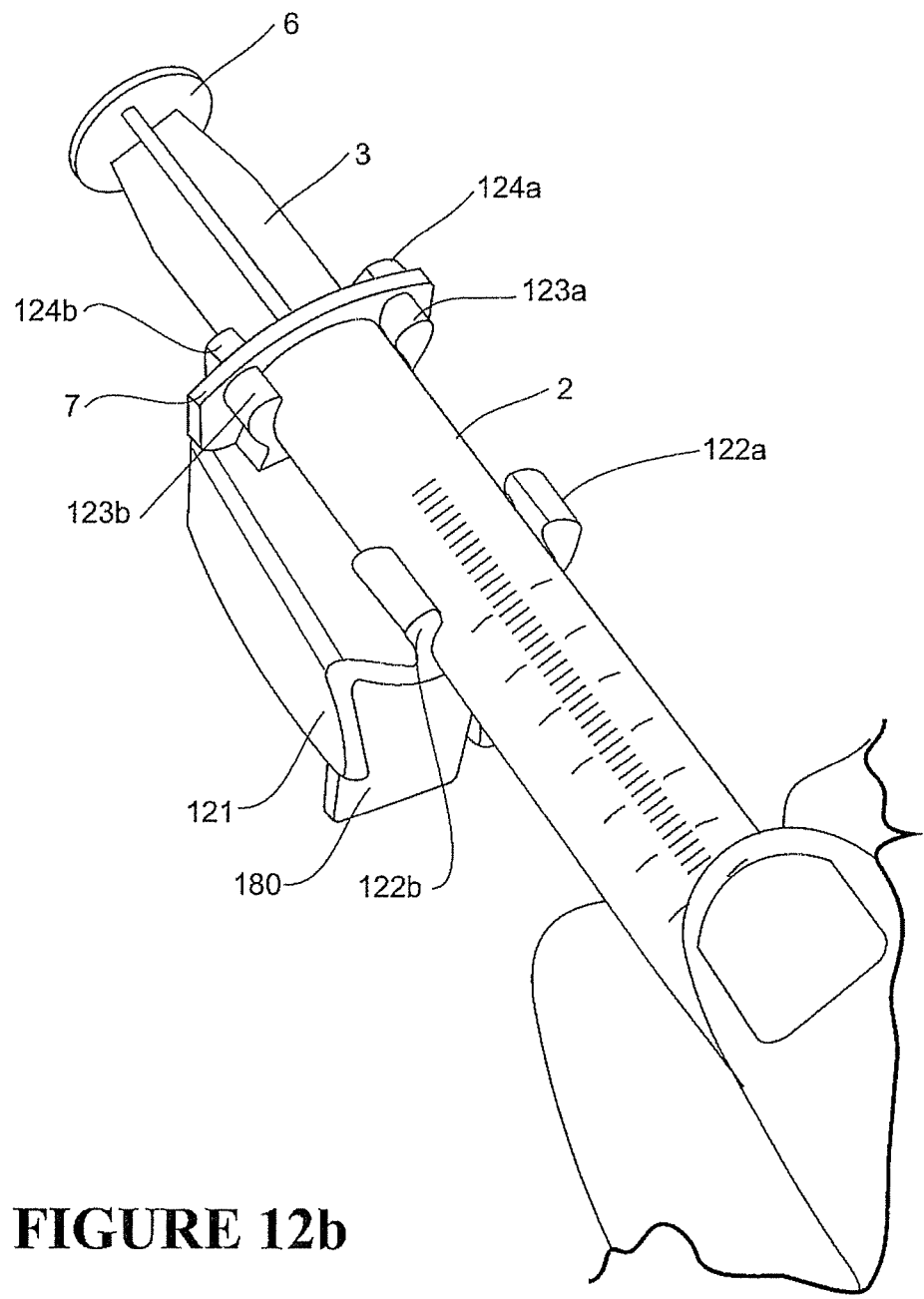
Figure 13:
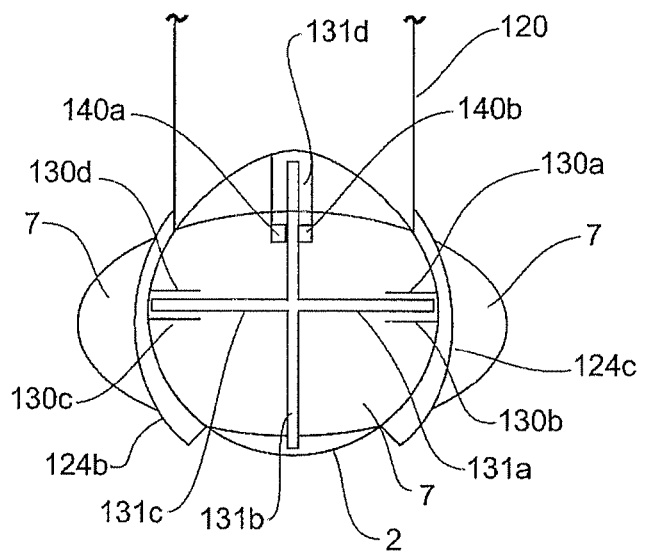
FIG. 13 is a plan view showing the optical reader attached to the syringe.

The syringe 1 is also adapted to be used with a detachable optical reader 120 for determining the quantity of liquid drug within the reservoir 2, as shown in FIGS. 12a to 13 FIG. 12a shows the reader 120 detached from the syringe 1, while FIG. 12b shows the reader 120 attached. The optical reader comprises a body portion 121 for retaining the required electronics for optical reading and clip means 122a-124b for attaching the optical reader 120 to the reservoir. The middle clips 123a, 123b are resilient and engage around the circumference of the reservoir below the flange 7. The top clips 124a, 124b sit above the flange 7 and resiliently clip around the cross arms of the plunger 6 (visible in FIG. 13) Similarly, the bottom clips 122a, 122b resiliently engage with the reservoir 2 further down its length. The reader 120 also comprises preferably two optical receivers 140 (one of which is visible in FIG. 13, the other is directly underneath and not visible), which might be photodiodes or similar. The plunger 63 is formed as a cross-shaped extrusion as shown in FIG. 13. The flange 6 is removed from FIG. 13 for clarity.

The plunger 3 comprises optically readable markings 82 on the flat face of at least one arm of the cross 131d (see e.g. FIG. 8). The optically readable markings 82 are preferably a plurality of markings positioned at least partially along the longitudinal length of the arm 131d. The known spacing or arrangement of the markings allow the position and/or direction of the plunger 3 to be determined. Preferably the markings are linearly arrange black bars 82. Alternatively, other types of optically readable markings can be used. The photodetectors e.g. 140 are arranged on the reader so they can detect the optical markings 82 on the plunger 3.

The markings 125 can be used to determine linear movement of the plunger. As the plunger 3 is moved downwards within the reservoir 2, the optical detectors 140 detect the bars on the plunger. The optical detectors detect each bar and feed this information into the electronics, which can count the number of bars to determine the position of the plunger 3 and thereby infer how far the plunger 3 has moved within the reservoir 2. The processor of the electronics determines position data from this. This in turn indicates the quantity of liquid drug remaining within the reservoir 2. That is, the longitudinal positional movement of the plunger 3 within the reservoir 2 defines a cavity in the reservoir for liquid. Therefore assuming there is no air space in that cavity, once the position of the plunger in its longitudinal position within the reservoir is known, the size of the cavity can be determined and therefore the amount of liquid therein. Therefore by counting the number of black bars that have passed the detectors, the longitudinal movement in the reservoir can be known. This works in both directions, therefore if the plunger is retracted back to increase the cavity size, by counting the number of bars the amount of retraction is known and therefore the cavity size and the amount of liquid.

Figure 15A:
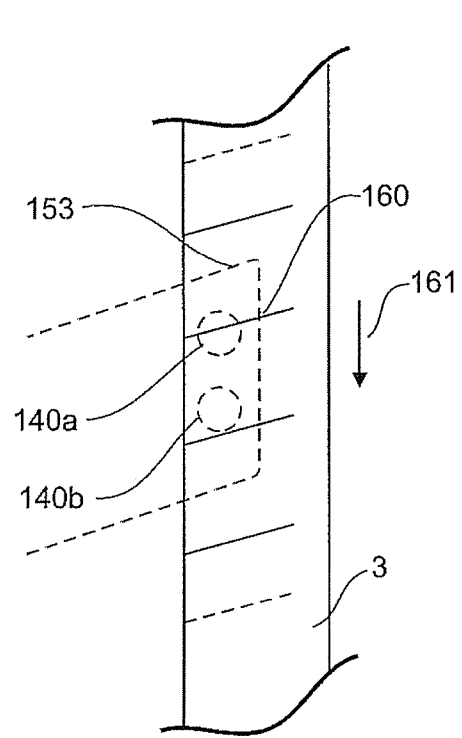
FIGS. 15a, 15b show the syringe markings and photodetectors in more detail.
Figure 15B:
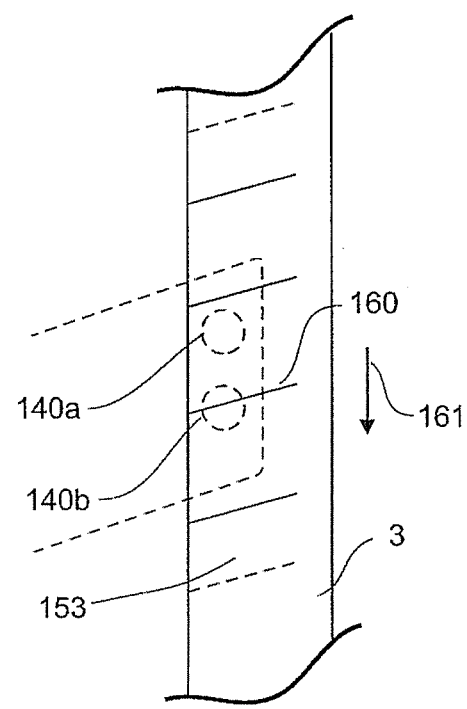
Figure 16:
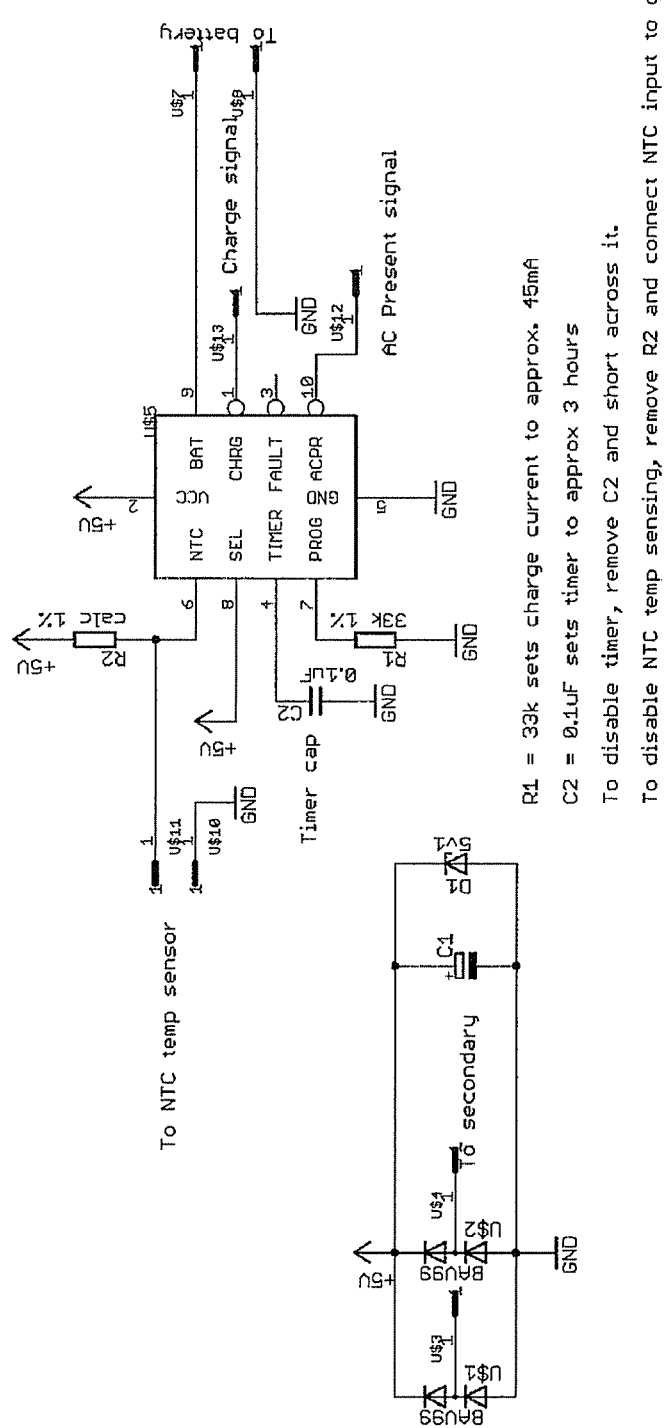
FIG. 16 is a circuit diagram of one embodiment of the inductive charger.
Figure 17:
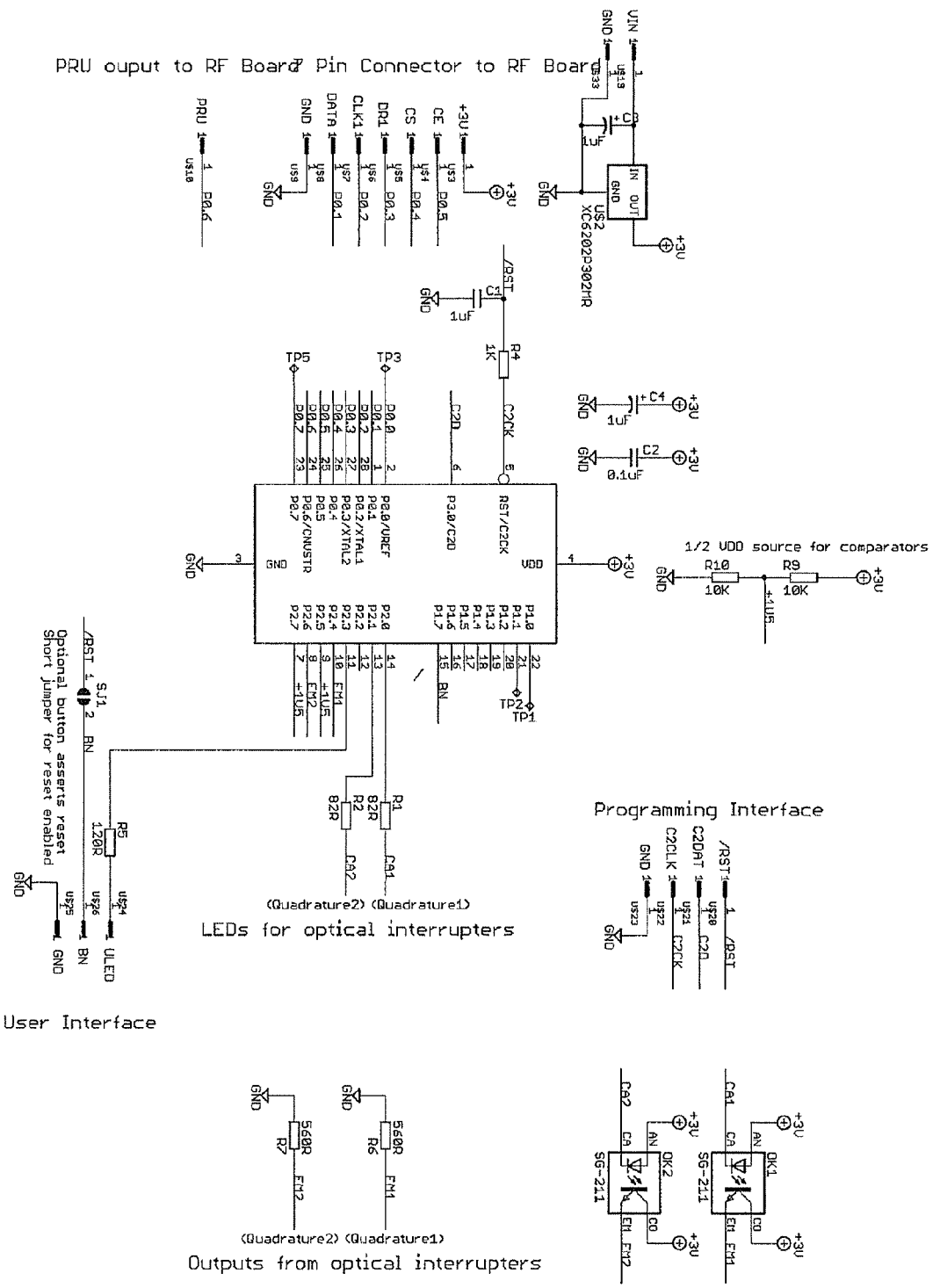
FIG. 17 is a circuit diagram of one embodiment of the quadrature detectors for the optical reader.

To enable determining the size of the cavity based on movement of the plunger 3 in both directions, two optical detectors are provided as shown in FIG. 15a, 15b. The use of two optical detectors enables quadrature encoding to allow the absolute position and direction of the plunger 3 movement to be determined. The use of quadrature encoding will be described in relation to FIGS. 15a, and 15b. A possible embodiment for the circuits of the quadrature detector are shown in FIG. 17 These Figures shown two spaced apart photodetectors 140a, 140b which individually can detect black bars on the plunger 3 and feed this information to the electronics, including the processor. From this the number of bars that have passed a detector can be counted and movement longitudinally of the plunger determined as described previously. Together the two photodetectors also provide information on which direction the plunger is moving.

As shown in FIG. 15a the first photodetector 140a is situated in a position such that it detects bar 160. The second photodetector 140b is in a position where it does not detect a bar. It should be noted that the photodetectors have to be spaced apart a different distance in the spacing between the bars such that the photodetectors do not detect bars or at least the edges of bars simultaneously. Next, as shown in FIG. 15b the plunger 3 has been moved such that bar 160 is now detected by the second photodetector 140b. At this point the first photodetector 140a does not detect any bar. Because the first photodetector 140a detected a bar and then second photodetector 140b detected a bar subsequently, (prior to photodetector a detecting any other bar) the electronics can infer that the direction of movement of the plunger is downwards as shown by the arrow 161. It can therefore know that as each detector detects a bar this means the volume of the cavity is decreasing by an amount proportional to the distance between the bars. Each time another bar is detected in this manner again the electronics can infer that the size of the cavity and the amount of liquid has again decreased by amount proportional to the distance between the bars. Those skilled in the art will know that the cavity size will be related to the diameter of the syringe and the distance between the bottom of the plunger 5 and the bottom of the syringe reservoir 2. The distance between the bottom of the plunger and the bottom of the syringe reservoir will be related to the movement of the syringe in the reservoir and therefore the position of the bars as they move past the detectors.

Similarly, quadrature encoding can determine when the syringe is moving in the opposite direction. When the syringe has moved upwards, the photodetectors 140a, 140b can detect the direction of movement and the number of bars they transverse indicates the increase in the size of the cavity between the bottom of the plunger and the bottom of the syringe reservoir. In turn this indicates the amount of liquid in the cavity if liquid is being drawn into the syringe through the needle.

The use of quantity analysis in this manner enables the quantity of liquid in the syringe to be determined when the syringe is actually being actuated. It is not necessary for the syringe to be installed in a holder. Therefore the syringe can provide continuous and real-time measurements of the quantity of liquid in the syringe.

The optical reader 120 can either be hard wired or preferably wirelessly connected to the spectral analyser to relay the quantity information. The optical reader 120 can also be attached and detached from the reservoir 2 as required. Other forms of optical markings and processing could be used to determine the extent that the plunger 3 has moved.

The optical reader 120 is moulded to also act as a holder to enable a person to use the device, for example as shown in FIG. 8. The reader 120 also comprises clip means 130a-130d extending from the upper resilient clips 124a, 124b as shown in FIG. 13. The clip means 130a-130d extend from the upper resilient arms 124a, 124b and engage with one or more of the flat arms 131a-131d of the extruded plunger 3. By doing so the clip means restricts rotational movement of the plunger 3, and allows the plunger to solely move in a linear manner. This ensures that the squared profiled plunger 95 extension portion will be received properly into the internal portion of the window 80 when the plunger 3 is forced downwards. Any rotation of the plunger 3 might prevent the plunger extension portion 95 extending into the window 80 and therefore prevent all liquid being expelled from the syringe 1. Alternatively, a flip disc that is hingeably connected to the syringe and that has openings corresponding to the cross arms of the plunger could be used. To prevent rotation of the plunger, the flip disc could be flipped about its hinge and snap locked onto the top of the plunger. This will prevent rotation but still allow longitudinal movement of the plunger.

Figure 14:
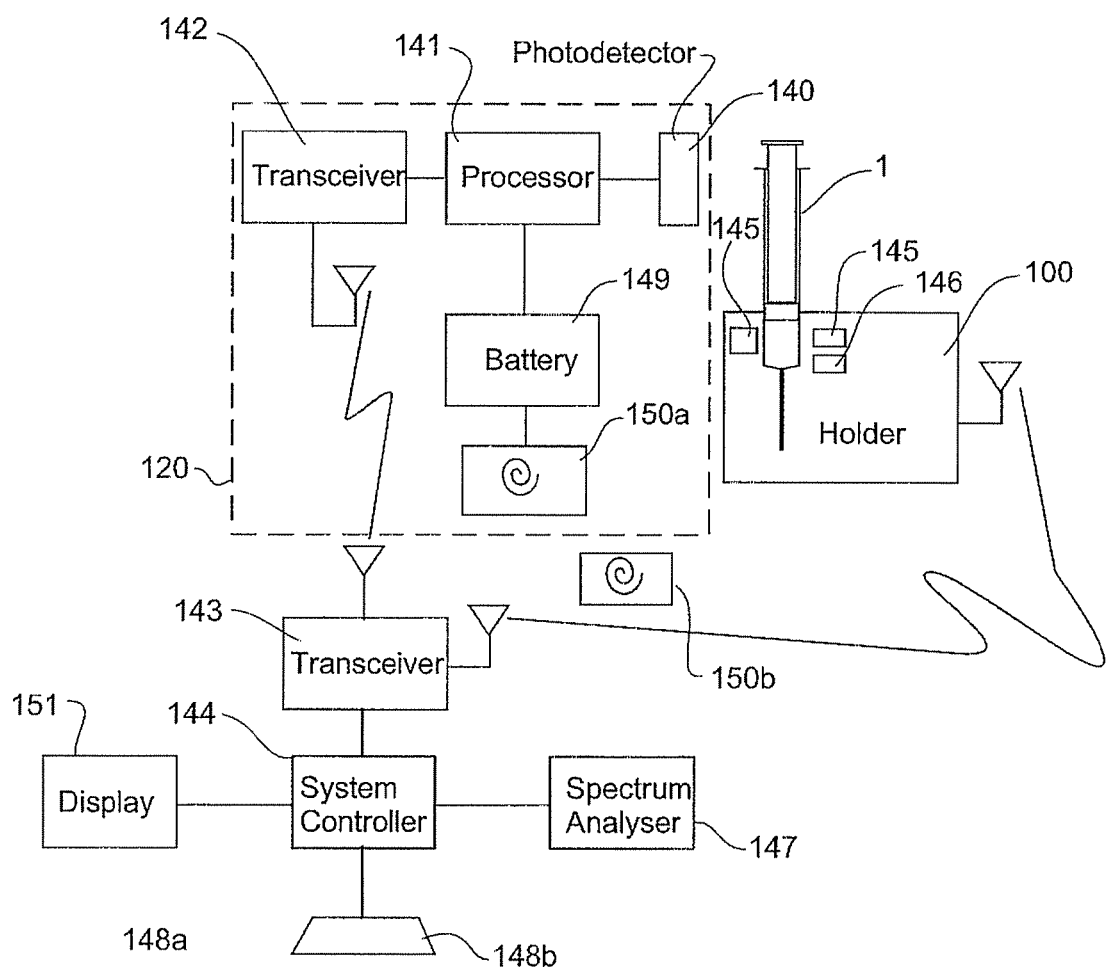
FIG. 14 is a schematic diagram of a qualitative and quantitative analysis system incorporating the syringe.

FIG. 14 shows a block diagram of the electronics in the optical reader 120. The photodetectors 140a, 140b, which are position on the clips 124a, 124b to detect the plunger markings 125, are connected to a processor 141. This could be a microprocessor, microcontroller or similar. The processor 141 receives information on the markings from the detectors 140, and from this determines the position of the plunger 3 within the reservoir 2 and the direction of movement. From this, the liquid quantity in the reservoir 2 can be inferred by the processor 141, or other system. The processor 141 is connected to a wireless transceiver 142 to transmit the quantitative analysis information (or information from which this analysis can be performed) to a computer system 151 via a transceiver 143, where the information can be used as required. The wireless transceiver 141 can any suitable type, such as an optical or radio (e.g. RF) transceiver. The electronics also comprises a battery 149 for powering the electronics, and an inductive coupler (150a in FIG. 14, 180 in FIG. 12b) for coupling the battery to an external inductive charging means (150b in FIG. 14, 181 in FIG. 12b). The secondary circuit of the inductive charger 180 is shown in FIG. 15. As shown in FIGS. 10b and 12b, the optical reader has an inductive charger coil 180 extending therefrom. When the syringe engages in the docking station as shown in FIG. 10b, the charger coil 180 extending from the reader will engage, abut or otherwise couple to the inductive charger coil 181 on the docking station to allow for inductive coupling and charging of the battery.

FIG. 14 shows in schematic form the overall system and indicates its overall functionality. The system is adapted for use with the syringe as described previously. The optical reader 120 with the photodetectors 140a, 140b is adapted for connection to the syringe. The optical quantitative analysis information it reads from the syringe 1 is processed and then the information sent to the computer system 151 via the wireless link transceiver 142. The processor 141 can process the optical information to infer quantitative analysis, or otherwise provide raw information which is then processed by the computer system 143151 (preferably located separated from the holder 100 and syringe 1). The system also includes the holder 100 for receiving the syringe 1. The holder includes a light source 146 for directing incident radiation onto the drug in the window of the installed syringe, and a sensor 145 (two alternatives shown) for sensing the received radiation that has been affected by the drug in the window. Alternatively, the light source and sensor are remotely positioned, and the light transferred to the holder using a suitable means. The sensed information is then transmitted, preferably wirelessly, via the transceiver 142 to the spectrum analyser 147 of the computer system 151. The spectrum analyser 147 determines the drug type from the spectral analysis information received from the sensor 145. A system controller 144 is connected to the analyser 147 and an audio device such as a speaker 148a and a display unit 148b. The system controller 147 receives spectrum data from the spectroscopic analyser and may compare this to stored "fingerprint" data from known liquid drugs to determine a best match drug. The display unit 148b and/or speaker 148a may then provide visual and/or audible information to a user of the drug which most closely matches the contents of the reservoir. Alternatively, the display device 148a could output a graphical display of the drugs liquid's photometric spectrum for review by the user. The system controller 144 also receives the quantity information and advises the user accordingly, and provides any alerts or warnings regarding the quantity of drug in the reservoir, or the quantity of drug administered to a patient. It will be appreciated by those skilled in the art that the quantitative and qualitative analysis information received from the holder 100 and optical reader 120 could be used in numerous ways to provide various checks and information to the user.

A method of use of the invention will now be described with reference to FIGS. 8 and 10a. Referring to FIG. 10a, the medic will first fill the reservoir 2 of the syringe 1 with the desired drug or other liquid and then position the plunger 3 so that it contains the correct quantity of the drug in accordance with the human readable markings 153 on the side of the syringe 1. The medic ensures that a portion of the drug sits within the window 80 of the syringe. The syringe is then docked into the docking station 100 by inserting the window 80 into the recess 110 and resting the cylinder of the syringe 1 on the support 103. If not done already, the terminations 105a, 105b of the holder 120 will be connected to an incident radiation source and an optical sensor respectively (shown schematically in FIG. 14). The optical sensor 145 may be hard wired directly to the spectrum analyser 147 and computer system or alternatively the information can be transmitted wirelessly to such a system. Alternatively, the affected radiation leaving the sample under observation might be optically transmitted to the spectrum analyser 147 either through fibre optic cable or wirelessly.

When the syringe 1 is installed, the drug within the window 80 will sit in the recess 110 within the optical path of the source radiation 146. The analyser system 147 can then be activated and a spectral reading taken from the incident radiation on the drug within the window 80. This can be processed in the usual way and the medic advised as necessary. Simultaneously, or at another suitable time the optical reader 120 is activated to read the markings 82 on the plunger of the syringe in order to determine quantitatively the amount of liquid within the syringe 1. This can be done in real-time such that a continuous or periodic quantity reading can be made as the plunger is moved. This is also transmitted wirelessly to the computer system 151a which uses the information and provides any warnings or advice to the medic as required. When the qualitative and quantitative analysis has been made, the medic can then remove the syringe 1 from the docking station 100. Note, the syringe does not have to be in the holder to take a quantity reading. The medic can then administer the drug to a patient by holding the device 1 as shown in FIG. 8 and pressing on the plunger 3 to expel the liquid from the syringe 1.

FIG. 8 shows the syringe in use. The user can attach the optical reader 120 to the reservoir 2 and then hold the syringe 1 by placing their forefinger under the curved surface of the bottom of the optical reader 120 and placing their thumb on the top 6 of the plunger 3. They can then inject the contents from the syringe 1 by pressing on the plunger 3 with their thumb in the usual manner. The plunger 3 will move downwards into the reservoir 2 and in doing so the optical markings 125 on the plunger 3 will pass the optical receptors 140 in the reader 120. As the markings 82 pass the optical receptors 140a, 140b the markings 82 are detected and the information passed to the processor 141, which determines the direction and extent of movement of the plunger 3 within the reservoir 2. This information can then be used to determine the quantity of liquid drug within the syringe as mentioned previously. This information can be used in any desired manner, such as providing a warning when too little or too much of a drug has been dispensed or providing any other useful information.

As noted, the syringe is adapted to be used in conjunction with a qualitative analysis device such as the spectroscopic analyser 147 to determine the composition of material within the reservoir. Accordingly, optical window 8 is manufactured within known optical and physical tolerances so that it has a known affect on radiation passing therethrough. The optical window section 80 will therefore cause a known reduction in light intensity at known frequencies and this effect can be factored in to calculations carried out by the spectroscopic analyser 147. The spectroscopic analyser may then determine an accurate spectroscopic "fingerprint" of the liquid within reservoir for comparison with spectroscopic data of known drugs. In this way, as a drug is being administered to a patient by the syringe or just prior to delivery of a drug using the syringe, it is possible to check that the drug being delivered is that which is intended to thereby avoid or reduce the risk of an adverse drug event.

Reflectance mode spectroscopic analysis may be carried out on the syringe by causing light, for example in the near-infrared (NIR) spectrum, to be incident on the optical window section 80. The incident light will be transmitted through the optical window section while being effected by the optical window section in a known way, interact with the contents within receptacle and then some of the incident light will be reflected back through the optical window section to a detector having been affected in a known way as it travels back through the optical window section.

Any suitable method of spectroscopic analysis could be used, for example those mentioned in relation to the first embodiment.

Alternatively, transmission mode spectroscopy could be employed to determine the composition of the contents of the reservoir.

While this is preferred a preferred embodiment, alternatives are possible. It will be appreciated that the window could comprise more than four panels (e.g., have hexagonal, octagonal profiles or the like), or the window could comprise less that four panels, such as three. One possibility is that the window could have one or two planar panels, with the remainder being formed as a circular shape, or some other non-planar shape. In such an embodiment, the recess in the stand would be shaped accordingly to receive the window, and the plunger extension as shaped accordingly.

The present invention provides a low cost and disposable liquid delivery device (such as a syringe) and associated spectroscopic system which enables a user to determine, at a patient's bedside whether a drug which is about to be injected is what is intended. As the syringe is disposable, it will only ever hold a single type of liquid and will not therefore suffer from contamination which could otherwise skew spectroscopic analysis results. The syringe is also advantageously portable and could even be utilised (to dispense liquids) whilst located within housing 12.

The invention claimed is:

1. A liquid delivery device for delivering a liquid drug to a patient or animal and adapted for facilitating drug analysis using NIR transmission spectrophotometry, the liquid delivery device comprising:
   an elongated reservoir comprising an elongated body having a first end and a second end adapted to contain liquid drug to be delivered, the reservoir having a luer connector disposed at the first end with a channel through which liquid drug may be dispensed,
   a liquid dispenser which causes a movement of the liquid drug from the reservoir to and through the channel in the luer connector,
   wherein the luer connector comprises first and second solid planar optical transparent sections arranged parallel on opposing sides of the channel, each transparent section being 0.8 to 1.2 mm thick and having predetermined optical and physical properties that allow electromagnetic radiation to pass through one of the transparent sections in a known manner into the interior of the channel and that allow such electromagnetic radiation affected by the liquid drug in the channel to pass through the other of the transparent sections as the affected electromagnetic radiation leaves the channel to facilitate analysis of he liquid drug in the channel using NIR transmission spectrophotometry,
   wherein the position of the transparent section allows contents of the channel to be analysed through the transparent sections using NIR transmission spectrophotometry when the liquid delivery device is docked end on.

2. A liquid delivery device according to claim 1 wherein the predetermined optical properties comprise optical density and clarity.

3. A liquid delivery device according to claim 1 wherein the transparent sections are formed from a material which is different from the material from which the remainder of the reservoir is formed.

4. A liquid delivery device according to claim 1 wherein the transparent sections comprise a transition portion between the reservoir elongated body and the luer connector wherein the luer connector has a smaller diameter than the diameter of the reservoir and wherein the transparent sections are provided in the transition portion.

5. A liquid delivery device according to claim 1 wherein to dock end on the first end is adapted to engage in a docking station comprising a receptacle adapted to receive the transparent sections, wherein the transparent sections are adapted to be received in the receptacle against a corresponding wall of the receptacle, the corresponding wall preventing rotation of the transparent sections received within the receptacle.

6. A liquid delivery device according to claim 5 wherein the docking station comprises an optical input for transmitting incident radiation to at least one of the transparent sections received in the receptacle, and an optical output for transmitting radiation received from at least one of the transparent sections received in the receptacle.

7. A liquid delivery device according claim 5 wherein at least one transparent section comprises a protrusion for engaging with a corresponding recess in the receptacle to prevent rotation of the at least one transparent section when received in the receptacle.

8. A liquid delivery device according to claim 1 further comprising optically readable markings on the liquid dispenser and an optical reader with one or more optical detectors arranged to detect the optically readable markings, wherein the optical reader comprises a processor that receives one or more signals from the one or more optical detectors and generates position data indicating a position of the liquid dispenser relative to the reservoir.

9. A liquid delivery device according to claim 7 wherein the processor generates quantity data indicating a quantity of the liquid drug in the reservoir.

10. A liquid delivery device according to claim 7 wherein optical reader comprises a transmitter adapted to wirelessly transmit the quantity data or position data to a system.

11. A liquid delivery device according to claim 7 wherein the optical reader further comprises an energy storage device for powering the optical reader, the energy storage device coupled to an inductive device, the inductive device adapted to inductively couple to an inductive recharging device to receive energy for recharging the energy storage device.

* * * * *